US010823944B2

(12) United States Patent
Tamura et al.

(10) Patent No.: US 10,823,944 B2
(45) Date of Patent: Nov. 3, 2020

(54) SURGICAL MICROSCOPE DEVICE AND SURGICAL MICROSCOPE SYSTEM

(71) Applicants: SONY OLYMPUS MEDICAL SOLUTIONS INC., Tokyo (JP); SONY CORPORATION, Tokyo (JP)

(72) Inventors: Shigeru Tamura, Tokyo (JP); Kenji Hirose, Tokyo (JP); Yoshiyuki Kamata, Tokyo (JP); Daisuke Iseki, Tokyo (JP)

(73) Assignees: SONY OLYMPUS MEDICAL SOLUTIONS INC., Tokyo (JP); SONY CORPORATION, Tokyo (JP)

(*) Notice: Subject to any disclaimer, the term of this patent is extended or adjusted under 35 U.S.C. 154(b) by 150 days.

(21) Appl. No.: 15/564,050

(22) PCT Filed: Apr. 7, 2016

(86) PCT No.: PCT/JP2016/061340
§ 371 (c)(1),
(2) Date: Oct. 3, 2017

(87) PCT Pub. No.: WO2016/181730
PCT Pub. Date: Nov. 17, 2016

(65) Prior Publication Data
US 2018/0100998 A1 Apr. 12, 2018

(30) Foreign Application Priority Data
May 14, 2015 (JP) .................... 2015-098678

(51) Int. Cl.
G02B 21/00 (2006.01)
G02B 21/24 (2006.01)
(Continued)

(52) U.S. Cl.
CPC .......... *G02B 21/0012* (2013.01); *A61B 90/20* (2016.02); *A61B 90/25* (2016.02);
(Continued)

(58) Field of Classification Search
CPC .... G02B 21/0012; G02B 21/24; G02B 21/36; G02B 21/361; G02B 21/362;
(Continued)

(56) References Cited

U.S. PATENT DOCUMENTS 5,346,459 A 9/1994 Allen
5,651,718 A 7/1997 Nakamura
(Continued)

FOREIGN PATENT DOCUMENTS

CN 1110864 A 10/1995
JP 8-266555 A 10/1996
(Continued)

OTHER PUBLICATIONS

International Search Report dated Jul. 12, 2016, in PCT/JP2016/061340, filed Apr. 7, 2016.
(Continued)

Primary Examiner — Stephone B Allen
Assistant Examiner — Adam W Booher
(74) Attorney, Agent, or Firm — Xsensus LLP

(57) ABSTRACT

By using a surgical microscope device, it becomes possible to continue surgery more reliably, even in the case in which the picture of the operating site is no longer displayed normally. Provided is a surgical microscope device including: a microscope unit (110) that images an observation target, and outputs a picture signal; a support unit (120) that supports the microscope unit, and is configured as a balance arm; and an auxiliary observation device (30) that is attachable to the microscope unit or the support unit. A manually operated manual brake mechanism (40) is provided with
(Continued)

respect to at least one of a plurality of rotation axis units constituting the support unit.

16 Claims, 7 Drawing Sheets

(51) Int. Cl.
| | |
|---|---|
| *A61B 90/25* | (2016.01) |
| *B25J 19/00* | (2006.01) |
| *A61B 90/20* | (2016.01) |
| *G02B 7/00* | (2006.01) |
| *G02B 21/36* | (2006.01) |
| *A61B 90/00* | (2016.01) |
| *A61B 90/50* | (2016.01) |

(52) U.S. Cl.
CPC ............... *A61B 90/37* (2016.02); *B25J 19/00* (2013.01); *G02B 7/001* (2013.01); *G02B 21/24* (2013.01); *G02B 21/361* (2013.01); *G02B 21/362* (2013.01); *G02B 21/368* (2013.01); *A61B 90/361* (2016.02); *A61B 2090/371* (2016.02); *A61B 2090/504* (2016.02); *A61B 2090/506* (2016.02); *A61B 2090/508* (2016.02); *A61B 2090/5025* (2016.02)

(58) Field of Classification Search
CPC ...... G02B 21/368; G02B 7/001; A61B 90/20; A61B 90/25; A61B 90/361; A61B 90/37; A61B 90/50; A61B 2090/371; A61B 2090/5025; A61B 2090/504; A61B 2090/506; A61B 2090/508; B25J 19/00; B25J 19/0004

See application file for complete search history.

(56) References Cited

U.S. PATENT DOCUMENTS

| | | |
|---|---|---|
| 5,812,301 A | 9/1998 | Nakamura |
| 5,851,216 A | 12/1998 | Allen |
| 2003/0117727 A1 | 6/2003 | Weber et al. |
| 2004/0104328 A1 | 6/2004 | Frick |
| 2009/0190209 A1* | 7/2009 | Nakamura ......... G02B 21/0012 359/375 |
| 2012/0320186 A1* | 12/2012 | Urban .................... A61B 34/30 348/79 |
| 2013/0327902 A1* | 12/2013 | Frick ...................... B25J 9/1065 248/122.1 |
| 2014/0157937 A1* | 6/2014 | Doi .................... F16M 11/2021 74/490.01 |
| 2016/0228205 A1* | 8/2016 | Nambi .................. A61B 34/72 |

FOREIGN PATENT DOCUMENTS

| | | |
|---|---|---|
| JP | 9-182759 A | 7/1997 |
| JP | 2003-98416 A | 4/2003 |
| JP | 3098905 U | 3/2004 |
| JP | 2005-6980 A | 1/2005 |
| JP | 2006-25912 A | 2/2006 |
| JP | 2008-23732 A | 2/2008 |
| WO | WO 94/28816 A1 | 12/1994 |

OTHER PUBLICATIONS

Extended European Search Report dated Dec. 6, 2018 in European Patent Application No. 16792455.4, 9 pages.
Chinese Office Action dated Nov. 1, 2019, issued in corresponding Chinese Patent Application No. 2016800262171.7.
Japanese Office Action dated Feb. 12, 2020, issued in corresponding Japanese Patent Application No. 2017-517827.

* cited by examiner

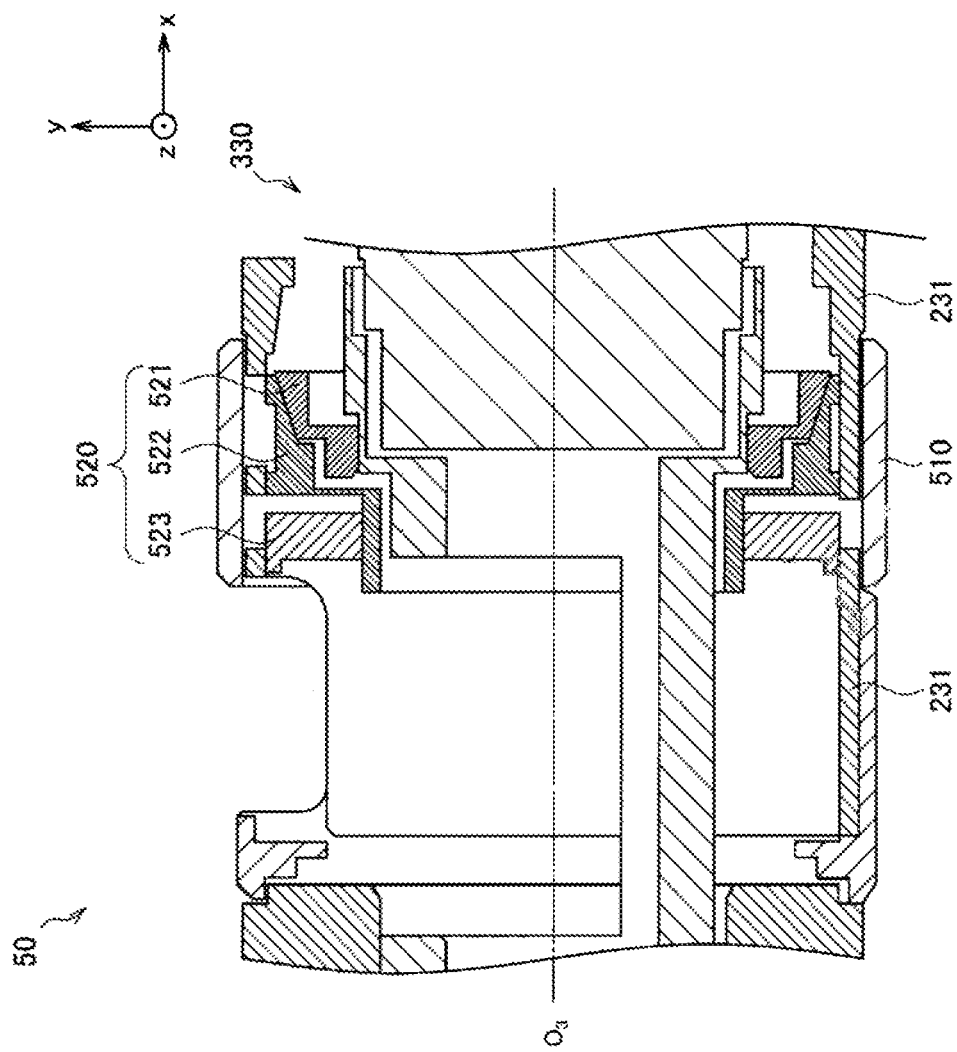

SURGICAL MICROSCOPE DEVICE AND SURGICAL MICROSCOPE SYSTEM

TECHNICAL FIELD

The present disclosure relates to a surgical microscope device and a surgical microscope system.

BACKGROUND ART

In the related art, in surgical operations targeting a fine region, such as neurosurgery, for example, a microscope device for enlarged observation of the operating site is used. The microscope device is made up of a microscope unit supported by an arm unit (support unit) (see Patent Literature 1 and 2, for example).

Since the operating site may be an extremely small region, there is demand for the microscope device to be capable of precisely adjusting the position of the microscope unit to observe a position desired by the surgeon. Consequently, as exemplified by the microscope devices described in Patent Literature 1 and 2, the support unit that supports the microscope unit in many cases is configured as a balance arm that includes a counter weight (counter balance). By configuring the support unit as a balance arm, the surgeon is able to move the microscope unit with a sensation as though operating the microscope unit in a weightless environment, and the operability for the surgeon can be improved.

CITATION LIST

Patent Literature

Patent Literature 1: JP H8-266555A
Patent Literature 2: JP 2005-6960A

DISCLOSURE OF INVENTION

Technical Problem

Herein, the microscope units in the microscope devices described in Patent Literature 1 and 2 are optical, and the surgeon observes the operating site by directly peering into an eyepiece provided on the microscope unit. Hereinafter, a microscope device provided with an optical microscope unit will also be called an optical microscope device for the sake of convenience.

Meanwhile, in recent years, there are being developed microscope devices provided with an electronic imaging microscope unit equipped with an image sensor and capable of imaging the operating site electronically. With a microscope device provided with an electronic imaging microscope unit (hereinafter also called an electronic imaging microscope device for the sake of convenience), a picture of the operating site imaged by the microscope unit is displayed on a display device installed in the operating room, and the surgeon performs surgery while observing the picture of the operating site depicted on the display device.

With such an electronic imaging microscope device, to increase patient safety further, it is desirable to surely enable the continuation of surgery even in cases in which the picture of the operating site is no longer displayed normally on the display device for some reason.

Accordingly, the present disclosure proposes a new and improved surgical microscope device and surgical microscope system enabling surgery to be continued more reliably even in the case in which the picture of the operating site is no longer displayed normally.

Solution to Problem

According to the present disclosure, there is provided a surgical microscope device including: a microscope unit that images an observation target, and outputs a picture signal; a support unit that supports the microscope unit, and is configured as a balance arm; and an auxiliary observation device that is attachable to the microscope unit or the support unit. A manually operated manual brake mechanism is provided with respect to at least one of a plurality of rotation axis units constituting the support unit.

In addition, according to the present disclosure, there is provided a surgical microscope system including: a microscope device that includes a microscope unit that images an observation target and outputs a picture signal, a support unit that supports the microscope unit and is configured as a balance arm, and an auxiliary observation device that is attachable to the microscope unit or the support unit; and a display device that displays a picture based on the picture signal. In the microscope device, a manually operated manual brake mechanism is provided with respect to at least one of a plurality of rotation axis units constituting the support unit.

According to the present disclosure, a microscope device includes an auxiliary observation device that is attachable to the microscope unit or the support unit. Consequently, by using the auxiliary observation device in the case in which the picture of the operating site is no longer displayed normally, surgery can be continued while observing the operating site directly. Also, in the microscope device, a manually operated manual brake mechanism is provided with respect to at least one of multiple rotation axis units constituting the support unit. Consequently, even in a case in which the balance of the support unit is lost due to the auxiliary observation device being attached, by causing the manual brake mechanism to operate, the attitude of the support unit can be maintained. Consequently, it becomes possible to continue surgery more reliably, even in the case in which the picture of the operating site is no longer displayed normally.

Advantageous Effects of Invention

According to the present disclosure as described above, it becomes possible to continue surgery more reliably, even in the case in which the picture of the operating site is no longer displayed normally. Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 7 is a cross-section diagram of a section corresponding to a manual brake mechanism in the second arm unit, the third rotation axis unit, and the third arm unit illustrated in FIG. 5.

MODE(S) FOR CARRYING OUT THE INVENTION

Figure 1:
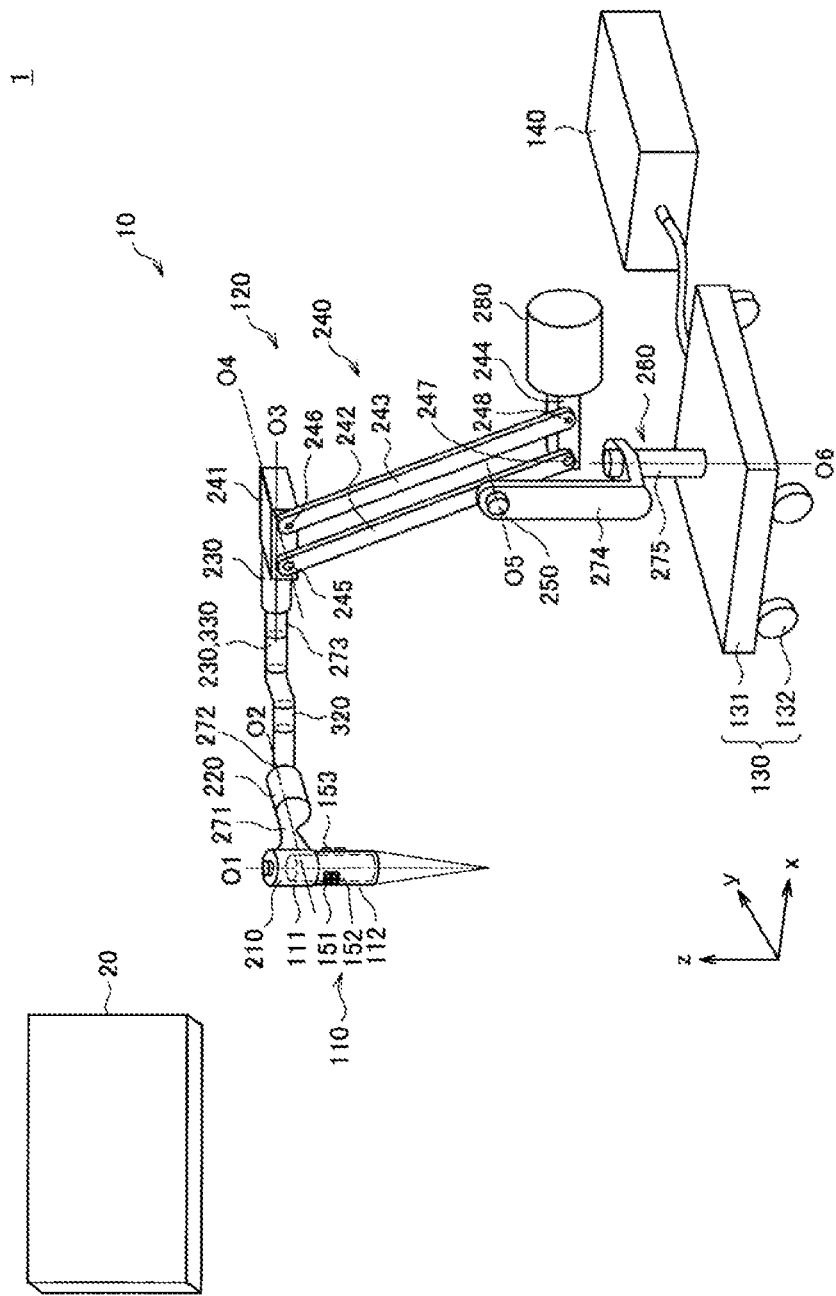
FIG. 1 is a diagram illustrating an exemplary configuration of a microscope system according to a first embodiment.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Hereinafter, the description will proceed in the following order.

1. First embodiment
1-1. Overall configuration of microscope device
1-2. Cases in which picture of operating site is no longer displayed normally
1-3. Configuration of manual brake mechanism
2. Second embodiment
2-1. Configuration of manual brake mechanism
3. Placement of manual brake mechanism
4. Supplemental remarks Note that in the following, the user who performs various operations on a microscope device according to the respective embodiments of the present disclosure is designated the surgeon for the sake of convenience. However, this designation does not limit the user who uses the microscope device, and the various operations on the microscope device may also be executed by any user, such as another member of the medical staff.

1. First Embodiment (1-1. Overall Configuration of Microscope Device)

With reference to FIG. 1, a configuration of a microscope system according to a first embodiment of the present disclosure will be described, and in addition, an overall configuration of a microscope device constituting such a microscope system will be described. FIG. 1 is a diagram illustrating an exemplary configuration of a microscope system according to a first embodiment.

Referring to FIG. 1, a microscope system 1 according to the first embodiment is made up of a microscope device 10 which supports a microscope unit 110 and which images an operating site of a patient with the microscope unit 110, and a display device 20 that displays a picture of the operating site imaged by the microscope device 10. During a surgery, the surgeon observes the operating site and performs various treatments on the operating site while referring to the picture imaged by the microscope device 10 and displayed on the display device 20.

(Display Device)

As described above, the display device 20 displays a picture of an operating site of a patient imaged by the microscope device 10. The display device 20 is installed in a location visible to the surgeon, such as on a wall of the operating room, for example. The type of the display device 20 is not particularly limited, and any of various known types of display devices may be used as the display device 20, such as a cathode ray tube (CRT) display device, a liquid crystal display device, a plasma display device, or an electroluminescence (EL) display device. Additionally, the display device 20 is not necessarily required to be installed inside the operating room, and may also be installed in a device used by being worn on the surgeon's body, such as a head-mounted display (HMD) or an eyeglasses-type wearable device.

(Microscope Device)

The microscope device 10 is provided with a microscope unit 110 for performing enlarged observation of an operating site of a patient, a support unit 120 (arm unit 120) that supports the microscope unit 110, a base unit 130 to which one end of the support unit 120 is connected and which supports the microscope unit 110 and the support unit 120, and a control device 140 that controls the operation of the microscope device 10. The microscope device 10 is a surgical microscope device for performing enlarged observation of an operating site of a patient during surgery.

(Base Unit 130)

The base unit 130 supports the microscope unit 110 and the support unit 120. The base unit 130 includes a platform 131 having a planar shape, and multiple casters 132 provided on the bottom face of the platform 131. One end of the support unit 120 is connected to the top face of the platform 131, while the microscope unit 110 is connected to the other end of the support unit 120 extending from the platform 131 (the front end). Also, the microscope device 10 is in contact with the floor through the casters 132, and is configured to be movable across the floor by the casters 132.

Note that in the following description, the vertical direction with respect to the floor on which the microscope device 10 is installed is defined to be the z-axis direction. The z-axis direction is also called the up-and-down direction or the vertical direction. Additionally, the two mutually orthogonal directions to the z-axis direction are defined to be the x-axis direction and the y-axis direction. The direction parallel to the x-y plane is also called the horizontal direction.

(Microscope Unit 110)

The microscope unit 110 is made up of a microscope body for performing enlarged observation of an operating site of a patient. In the illustrated example, the optical axis direction of the microscope unit 110 is approximately aligned with the z-axis direction. The microscope unit 110 has a configuration corresponding to an electronic imaging microscope unit, and is made up of a barrel unit 112 having an approximately hollow round cylindrical shape, and an imaging unit 111 provided inside the barrel unit 112. Additionally, the imaging unit 111 is made up of an optical system such as an objective lens and a zoom lens, and an image sensor that captures an image of a subject (namely, the operating site) with light passing through the optical system.

The aperture on the bottom end of the barrel unit 112 is provided with a cover glass for protecting the imaging unit 111. A light source is also provided inside the barrel unit 112, and during imaging, the subject is irradiated with illuminating light radiating from the light source through the cover glass. Of this illuminating light, the light reflecting back from the subject is incident on the imaging unit 111 via the cover glass, and as a result, a signal indicating an image of the operating site (picture signal) is acquired by the imaging unit 111.

For the microscope unit 110, it is sufficient to apply a configuration corresponding to any of various known types of electronic imaging microscope units, and for this reason a detailed description thereof will be reduced or omitted herein. For example, any of various known types of image sensors may be applied as the image sensor of the imaging unit 111, such as a charge-coupled device (CCD) sensor or a complementary metal-oxide-semiconductor (CMOS) sensor. Additionally, the imaging unit 111 may also be configured as a stereo camera equipped with a pair of image sensors. Also, any of various known types of configurations may be applied to the optical system of the imaging unit 111. Furthermore, any of various types of functions typically provided in electronic imaging microscope units, such as an autofocus (AF) function and an optical zoom function, may be provided in the imaging unit 111.

The picture signal acquired by the microscope unit 110 is transmitted to the control device 140. In the control device 140, various types of image processing are performed, such as gamma correction and white balance adjustment, for example. In addition, in the control device 140, image processing such as enlargement and pixel interpolation related to an electronic zoom function may also be performed. The picture signal that has been subjected to image processing is transmitted to the display device 20 provided in the operating room, and a picture of the surgical site is displayed on the display device 20, appropriately magnified at a desired magnification by an optical zoom function and/or an electronic zoom function, for example. Note that the communication between the control device 140 and the display device 20 may be realized by any of various known wired or wireless methods.

Note that a processing circuit for performing the above image processing may be provided in the microscope unit 110, and the above image processing may be performed by the processing circuit of the microscope unit 110, without being performed by the control device 140. In this case, image information after suitable image processing has been performed in the processing circuit provided in the microscope unit 110 may be transmitted from the microscope unit 110 to the display device 20 provided in the operating room. Also, in this case, the communication between the microscope unit 110 and the display device 20 may be realized by any of various known wired or wireless methods.

Figure 2:
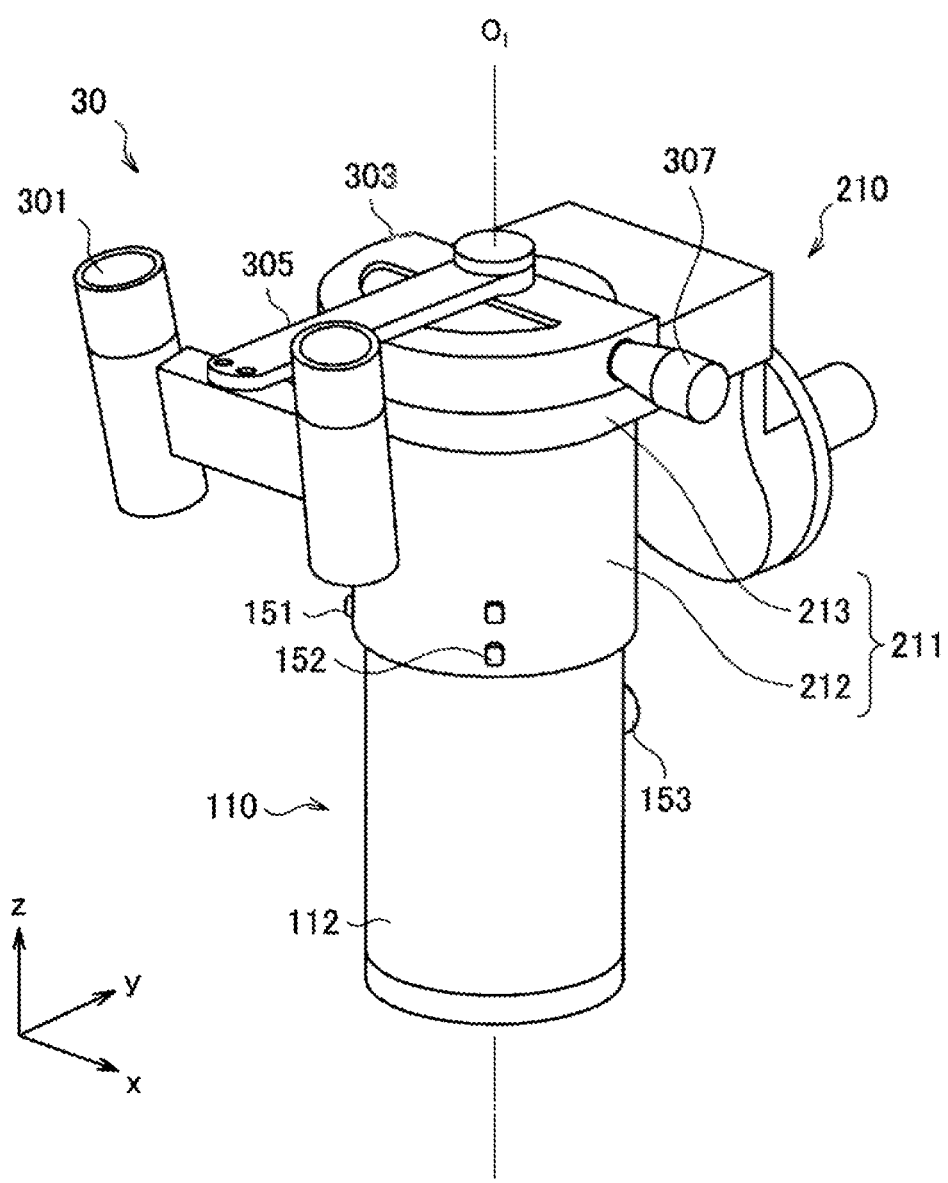
FIG. 2 is a diagram illustrating a state in which an auxiliary observation device is attached to a first rotation axis unit.

The microscope unit 110 is provided with various types of switches for controlling the operation of the microscope unit 110, at an outer side face thereof. For example, the microscope unit 110 is provided with a zoom switch 151 (zoom SW 151) and a focus switch 152 (focus SW 152) for adjusting the imaging parameters of the microscope unit 110, as well as an operating mode toggle switch 153 (operation mode toggle SW 153) for toggling the operating mode of the support unit 120. Note that FIG. 1 illustrates the zoom SW 151 and the focus SW 152 arranged on the outer side face of the barrel unit 112 for the sake of convenience, but in the first embodiment, these switches may also be provided on the outer side face of an approximately hollow round cylindrical housing constituting a first rotation axis unit 210, as illustrated in FIG. 2 described later.

The surgeon, by operating the zoom SW 151 and the focus SW 152, is able to adjust the magnification and the focal length of the microscope unit 110, respectively. Also, by operating the operating mode toggle SW 153, the surgeon is able to toggle the operating mode of the support unit 120 between a locked mode and a free mode.

Herein, the locked mode is an operating mode in which the position and the attitude of the microscope unit 110 are locked by using a brake to restrain rotation about each rotation axis provided in the support unit 120. The free mode is an operating mode in which the brake is released, thereby allowing free rotation about each rotation axis provided in the support unit 120, and enabling the surgeon to adjust the position and the attitude of the microscope unit 110 with direct operations. Herein, direct operations mean operations in which the surgeon grips the microscope unit 110 with his or her hand, for example, and directly moves the microscope unit 110. For example, the operating mode of the support unit 120 becomes the free mode while the surgeon is pressing the operating mode toggle SW 153, and the operating mode of the support unit 120 becomes the locked mode while the surgeon releases his or her hand from the operating mode toggle SW 153.

Note that these switches are not necessarily required to be provided on the microscope unit 110. In the first embodiment, it is sufficient for the microscope device 10 to be provided with a mechanism for accepting operating input having functions similar to these switches, and the specific configuration of such a mechanism is not limited. For example, these switches may also be provided on another section of the microscope device 10. As another example, an input device such as a remote control may be used, and commands corresponding to these switches may be input into the microscope device 10 remotely.

Also, although the barrel unit 112 of the microscope unit 110 is illustrated as a simple hollow round cylindrical member in FIG. 1 for the sake of simplicity, in actuality, the barrel unit 112 may also be shaped innovatively to be gripped more easily by the surgeon. For example, when in the free mode, operations of moving the microscope unit 110 with the surgeon gripping the barrel unit 112 directly in hand may be anticipated. At this point, since the surgeon performs an operation of moving the microscope unit 110 while pressing the operating mode toggle SW 153, the shape of the barrel unit 112 and the placement of the operating mode toggle SW 153 may be decided appropriately with consideration for operability by the surgeon while in the free mode. In addition, the placement of the zoom SW 151 and the focus SW 152 may be decided appropriately with similar consideration for operability by the surgeon.

(Control Device 140)

The control device 140 is made up of a processor, such as a central processing unit (CPU) or a digital signal processor (DSP), for example, or a control board on which these processors are mounted together with components such as memory. By executing computational processing according to a certain program, the control device 140 controls the operation of the microscope device 10.

For example, the control device 140 includes a function of toggling the operating mode of the support unit 120 described above by controlling the driving of the brake provided in each joint unit of the support unit 120 in response to operating input performed by the surgeon via the above operating mode toggle SW 153. As another example, the control device 140 includes a function of appropriately driving the optical system in the imaging unit 111 of the microscope unit 110 to adjust the magnification and the focal length of the microscope unit 110 in response to operating input performed by the surgeon via the above zoom SW 151 and focus SW 152. In addition, the control device 140 includes a function of performing various types of image processing on a picture signal imaged by the microscope unit 110, and transmitting the processed picture signal to the display device 20 provided in the operating room.

Note that in the illustrated example, the control device 140 is provided as a different configuration from the microscope unit 110, the support unit 120, and the base unit 130, and is connected to the base unit 130 by a cable. However, the first embodiment is not limited to such an example. For example, a processor, a control board, or the like that realizes functions similar to the control device 140 may also be disposed inside the base unit 130. Additionally, by incorporating a processor, a control board, or the like that realizes functions similar to the control device 140 into the microscope unit 110 internally, the control device 140 and the microscope unit 110 may be configured in an integrated manner.

(Support Unit 120)

The support unit 120 holds the microscope unit 110, and moves the microscope unit 110 three-dimensionally while also locking the position and the attitude of the microscope unit 110 after moving. In the first embodiment, the support unit 120 is configured as a balance arm having six degrees of freedom. However, the first embodiment is not limited to such an example, and the support unit 120 may also be configured to have a different number of degrees of freedom. By configuring the support unit 120 as a balance arm and taking a configuration having an equilibrium of moments for the microscope unit 110 and the support unit 120 as a whole, it becomes possible to move the microscope unit 110 with less external force, and operability for the surgeon can be improved further.

The support unit 120 is provided with six rotation axes corresponding to the six degrees of freedom (first axis $O_1$, second axis $O_2$, third axis $O_3$, fourth axis $O_4$, fifth axis $O_5$, and sixth axis $O_6$). In the following description, for the sake of convenience, the members constituting each rotation axis will be referred to collectively as the rotation axis unit. For example, the rotation axis unit may be made up of components such as a bearing, a shaft rotatably inserted into the bearing, and a brake that restrains rotation about the rotation axis. The parallelogram link mechanism 240 described later may also be considered to be one of the rotation axis units.

The support unit 120 is made up of a first rotation axis unit 210, a second rotation axis unit 220, a third rotation axis unit 230, a fourth rotation axis unit 240, a fifth rotation axis unit 250, and a sixth rotation axis unit 260 corresponding to each rotation axis, a first arm unit 271, a second arm unit 272, a third arm unit 273, a fourth arm unit 274, and a fifth arm unit 275 rotatably connected to each other by the first rotation axis unit 210 to the sixth rotation axis unit 260, and a counterweight 280 for maintaining the equilibrium of moments for the microscope unit 110 and the support unit 120 as a whole. Note that the fourth rotation axis unit 240 corresponds to the parallelogram link mechanism 240.

Note that in the following description, when describing the configuration of the support unit 120, the side on which the microscope unit 110 is provided may also be called the front end side or the front end unit, while the side near the base unit 130 may also be called the base end side or the base end unit.

The first rotation axis unit 210 has an approximately hollow round cylindrical shape, and is connected to the base end unit of the barrel unit 112 of the microscope unit 110 so that the central axis is approximately aligned with the central axis of the barrel unit 112 of the microscope unit 110. The first rotation axis unit 210 rotatably supports the microscope unit 110, with the rotation axis direction (first axis $O_1$ direction) being a direction approximately aligned with the optical axis of the microscope unit 110. In the example illustrated in FIG. 1, the first axis $O_1$ is provided as a rotation axis approximately parallel to the z-axis. By having the microscope unit 110 rotate about the first axis $O_1$ by the first rotation axis unit 210, the direction of images captured by the microscope unit 110 is adjusted.

Note that in the illustrated example, part of the imaging unit 11 of the microscope unit 110 is stored inside the substantially hollow round cylindrical housing constituting the first rotation axis unit 210. In other words, the microscope unit 110 and the first rotation axis unit 210 are configured as an integrated member. However, the first embodiment is not limited to such an example, and the first rotation axis unit 210 and the microscope unit 110 may also be configured as mutually individual members.

The front end of the first arm unit 271 extending in a direction approximately perpendicular to the first axis $O_1$ is connected to the first rotation axis unit 210. Also, at the base end of the first arm unit 271, there is provided the second rotation axis unit 220 that rotatably supports the first arm unit 271, with the rotation axis direction (second axis $O_2$ direction) being a direction approximately parallel to the extension direction of the first arm unit 271. The second axis $O_2$ is a rotation axis approximately perpendicular to the first axis $O_1$, and in the example illustrated in FIG. 1, is provided as a rotation axis approximately parallel to the y-axis. By having the microscope unit 110 and the first arm unit 271 rotate about the second axis $O_2$ as a rotation axis by the second rotation axis unit 220, the position in the x-axis direction of the microscope unit 110 is adjusted.

The front end of the second arm unit 272 extending in a direction approximately perpendicular to both the first axis $O_1$ and the second axis $O_2$ is connected to the second rotation axis unit 220. Also, at the base end of the second arm unit 272, there is provided the third rotation axis unit 230 that rotatably supports the second arm unit 272, with the rotation axis direction (third axis $O_3$ direction) being a direction approximately parallel to the extension direction of the second arm unit 272. The third axis $O_3$ is a rotation axis approximately perpendicular to the first axis $O_1$ and the second axis $O_2$, and in the example illustrated in FIG. 1, is provided as a rotation axis approximately parallel to the x-axis. By having the microscope unit 110, the first arm unit 271, and the second arm unit 272 rotate about the third axis $O_3$ as a rotation axis by the third rotation axis unit 230, the position in the y-axis direction of the microscope unit 110 is adjusted.

In this way, the support unit 120 is configured so that as a result of rotation about the second axis $O_2$ and the third axis $O_3$ being controlled respectively, the attitude of the microscope unit 110 is controlled. In other words, the second rotation axis unit 220 and the third rotation axis unit 230 may be the rotation axis units that prescribe the attitude of the microscope unit 110.

Note that in the first embodiment, the second arm unit 272 is provided with a manually operated manual brake mechanism for stopping rotation in the second rotation axis unit 220 and the third rotation axis unit 230 during an emergency. The configuration of the second arm unit 272 and the manual brake mechanism will be described further in (1-3. Configuration of manual brake mechanism) below.

The front end of the third arm unit 273 extending in a direction approximately parallel to the third axis $O_3$ is connected to the third rotation axis unit 230. Also, the front end of the top side of the parallelogram link mechanism 240 is connected to the base end of the third arm unit 273.

The parallelogram link mechanism 240 is made up of four arms (arms 241, 242, 243, and 244) arranged in a parallelogram shape, and four joint units (joint units 245, 246, 247, and 248) respectively provided at positions corresponding to the approximate vertices of the parallelogram.

The front end of the arm 241 extending in a direction approximately parallel to the third axis $O_3$ is connected to the base end of the third arm unit 273. The joint unit 245 is provided near the front end of the arm 241, while the joint unit 246 is provided near the base end of the arm 241. The front ends of the arms 242 and 243 are connected to the joint units 245 and 246, respectively, allowing rotation about respective rotation axes (fourth axis $O_4$) approximately perpendicular to the extension direction of the arm 241 and approximately parallel to each other. Furthermore, the joint units 247 and 248 are provided on the base ends of the arms 242 and 243, respectively. The front end and the base end of the arm 244 are connected to these joint units 247 and 248, respectively, allowing rotation about the fourth axis $O_4$, and also approximately parallel to the arm 241.

In this way, the four joint units constituting the parallelogram link mechanism 240 include rotation axes (fourth axis $O_4$) approximately parallel to each other and approximately in the same direction, which operate in conjunction with each other about the fourth axis $O_4$. In the example illustrated in FIG. 1, the fourth axis $O_4$ is provided as a rotation axis approximately parallel to the y-axis. In other words, the parallelogram link mechanism 240 includes multiple joint units that rotate in conjunction with each other around rotation axes disposed in mutually different positions but in the same direction, and fulfills the role of a transmission mechanism that transmits an operation on one end to the other end. By providing the parallelogram link mechanism 240, the motion of the configuration on the front end side past the parallelogram link mechanism 240 (that is, the microscope unit 110, the first rotation axis unit 210, the second rotation axis unit 220, the third rotation axis unit 230, the first arm unit 271, the second arm unit 272, and the third arm unit 273) is transmitted to the base end side of the parallelogram link mechanism 240.

On a part of the arm 242 separated a certain distance from the base end, there is provided the fifth rotation axis unit 250 that rotatably supports the parallelogram link mechanism 240, with the rotation axis direction (fifth axis $O_5$ direction) being a direction perpendicular to the extension direction of the arm 242. The fifth axis $O_5$ is a rotation axis approximately parallel to the fourth axis $O_4$, and in the example illustrated in FIG. 1, is provided as a rotation axis approximately parallel to the y-axis. The front end of the fourth arm unit 274 running in the z-axis direction is connected to the fifth rotation axis unit 250, and the microscope unit 110, the first arm unit 271, the second arm unit 272, the third arm unit 273, and the parallelogram link mechanism 240 are allowed to rotate with respect to the fourth arm unit 274 via the fifth rotation axis unit 250, about the fifth axis $O_5$ as the rotation axis.

The fourth arm unit 274 is approximately L-shaped, with the base end side bent to be approximately parallel to the floor. The sixth rotation axis unit 260 that allows the fourth arm unit 274 to rotate about a rotation axis (sixth axis $O_6$) parallel to the vertical direction is connected to the face approximately parallel to the floor on the fourth arm unit 274.

In the illustrated example, the sixth rotation axis unit 260 is integrated with the fifth arm unit 275 that extends in the vertical direction. In other words, the front end of the fifth arm unit 275 is connected to the face approximately parallel to the floor on the base end of the fourth arm unit 274. Also, the base end of the fifth arm unit 275 is connected to the top face of the platform 131 of the base unit 130. With this configuration, the microscope unit 110, the first arm unit 271, the second arm unit 272, the third arm unit 273, the parallelogram link mechanism 240, and the fourth arm unit 274 rotate with respect to the base unit 130 via the sixth rotation axis unit 260, about the sixth axis $O_6$ as the rotation axis.

The arm 244 constituting the bottom side of the parallelogram link mechanism 240 is formed to be longer than the arm 241 constituting the top side, and the end of the arm 242 which is positioned diagonally opposite the part where the third rotation axis unit 230 is connected on the parallelogram link mechanism 240 is extended to the outside of the parallelogram link mechanism 240. On the extended end of the arm 244, the counterweight 280 is provided. The mass and the placement of the counterweight 280 are adjusted so that the rotation moment produced about the fourth axis $O_4$ and the rotation moment produced about the fifth axis $O_5$ may be canceled out by the mass of the configuration disposed past the front end side of the counterweight 280 itself (that is, the microscope unit 110, the first rotation axis unit 210, the second rotation axis unit 220, the third rotation axis unit 230, the first arm unit 271, the second arm unit 272, the third arm unit 273, and the parallelogram link mechanism 240).

In addition, the placement of the fifth rotation axis unit 250 is adjusted so that the center of gravity of the configuration disposed farther on the front end side than the fifth rotation axis unit 250 is positioned on the fifth axis $O_5$. Furthermore, the placement of the sixth rotation axis unit 260 is adjusted so that the center of gravity of the configuration disposed farther on the front end side than the sixth rotation axis unit 260 is positioned on the sixth axis $O_6$.

By configuring the mass and placement of the counterweight 280, the placement of the fifth rotation axis unit 250, and the placement of the sixth rotation axis unit 260 in this way, the support unit 120 may be configured as a balance arm that maintains the equilibrium of moments for the microscope unit 110 and the support unit 120 as a whole. By configuring the support unit 120 as a balance arm, in the case in which the surgeon attempts to move the microscope unit 110 with a direct operation, the surgeon becomes able to move the microscope unit 110 with less external force, almost like a weightless state. Consequently, user operability can be improved.

Herein, in the first embodiment, the second rotation axis unit 220 and the third rotation axis unit 230 are provided with actuators 320 and 330 for imparting driving force with respect to rotation about the second axis $O_2$ and the third axis $O_3$, respectively. The rotation of members about the second axis $O_2$ and the third axis $O_3$ in the support unit 120 is driven by the actuators 320 and 330, respectively.

The driving of the actuators 320 and 330 is controlled by the control device 140. For example, when an instruction to switch the operating mode of the support unit 120 to the locked mode is input via the operating mode toggle SW 153 described above, the control device 140 drives the actuators 320 and 330 so that the second rotation axis unit 220 and the third rotation axis unit 230 do not rotate. In this way, brakes for stopping the rotation of the second rotation axis unit 220 and the third rotation axis unit 230 are realized by the driving forces provided by the actuators 320 and 330.

Also, the actuators 320 and the 330 are provided with torque sensors for detecting the force (torque) acting on the second rotation axis unit 220 and the third rotation axis unit 230, respectively, and on the basis of detection values from these torque sensors, the control device 140 can appropriately control the driving of the actuators 320 and 330. For example, when an instruction to switch the operating mode of the support unit 120 to the free mode is input via the operating mode toggle SW 153 described above, the control device 140 drives the actuators 320 and 330 to support forces causing the second rotation axis unit 220 and the third rotation axis unit 230 to rotate, which are imparted as a result of the surgeon attempting to move the microscope unit 110. In other words, the control device 140 is able to drive the actuators 320 and 330 to realize what is called a power assist operation. With this arrangement, during the free mode, the surgeon becomes able to move the microscope unit 110 with less force, and operability for the surgeon is improved further.

Note that typical force control can be used for the driving control of the actuators 320 and 330. For example, the power assist operation described above is an operation widely conducted in devices driven by force control. Consequently, herein, a detailed description of specific methods of the driving control of the actuators 320 and 330 is omitted.

Meanwhile, the first rotation axis unit 210, the fourth rotation axis unit 240, the fifth rotation axis unit 250, and the sixth rotation axis unit 260 are provided with a brake mechanism (not illustrated) that restrains rotation about the first axis $O_1$, the fourth axis $O_4$, the fifth axis $O_5$ and the sixth axis $O_6$, respectively. Note that in the fourth rotation axis unit 240, that is, in the parallelogram link mechanism 240, since the four joint units (joint units 245, 246, 247, and 248) rotate in conjunction with each other, it is sufficient to provide a brake mechanism on at least one of these joint units 245, 246, 247, and 248 for the parallelogram link mechanism 240.

The driving of these brake mechanisms is controlled by the control device 140. When an instruction to switch the operating mode of the support unit 120 to the locked mode is input via the operating mode toggle SW 153, by control from the control device 140, these brake mechanisms are activated all at once, and each of the corresponding rotation axes is restrained. Also, when an instruction to switch the operating mode of the support unit 120 to the free mode is input via the operating mode toggle SW 153, by control from the control device 140, these brake mechanisms are released all at once. Note that to distinguish from the manual brake mechanism described later, in the following description, these brake mechanisms that operate by control from the control device 140 will be designated the electronically controlled brake mechanisms for the sake of convenience.

For these electronically controlled brake mechanisms, a mechanism in which the brake is released when an electric current is present and the brake is applied when an electric current is not present, such as a non-excitation (negative actuation) electromagnetic brake, is used favorably. With this arrangement, it becomes possible for the support unit 120 to maintain attitude, even during an emergency such as a power failure. However, the first embodiment is not limited to such an example, and any of various types of brake mechanisms used in typical balance arms may be applied as these electronically controlled brake mechanisms. For example, these electronically controlled brake mechanisms may be electromagnetic brakes, or may be mechanically driven.

In this way, in the first embodiment, the second rotation axis unit 220 and the third rotation axis unit 230 are driven by the actuators 320 and 330, respectively, and likewise when locking attitude, the rotation of the second rotation axis unit 220 and the third rotation axis unit 230 is locked by these actuators 320 and 330. In other words, the second rotation axis unit 220 and the third rotation axis unit 230 are not provided with electronically controlled brake mechanisms.

The second rotation axis unit 220 and the third rotation axis unit 230 are the rotation axis units that prescribe the attitude of the microscope unit 110, and are rotation axes disposed comparatively near the microscope unit 110. Consequently, by not providing electronically controlled brake mechanisms and only providing actuators in the second rotation axis unit 220 and the third rotation axis unit 230, the configuration of the second rotation axis unit 220 and the third rotation axis unit 230 can be miniaturized, and the configuration near the microscope unit 110 can be miniaturized. By miniaturizing the configuration near the microscope unit 110, it becomes possible to secure more work space for the surgeon. Also, as described above, in the microscope system 1, the surgeon performs surgery while referring to a picture of the operating site displayed on the display device 20. Consequently, by miniaturizing the configuration near the microscope unit 110, it becomes possible to secure a greater field of view for the surgeon looking at the display device 20. Thus, a microscope device 10 that is easier to use by the surgeon may be provided.

Additionally, in the case in which a non-excitation (negative actuation) electromagnetic brake is used as the electronically controlled brake mechanism of each rotation axis unit, for example, an electric current must be supplied continuously to the electromagnetic brake while the electromagnetic brake is released, and thus increased power consumption is a concern. Additionally, an increase in the amount of heat produced in the support unit 120 due to the supply of electric current is also a concern. Like in the first embodiment, by configuring the support unit 120 so that an electronically controlled brake mechanism is not provided in some of the rotation axis units (namely the second rotation axis unit 220 and the third rotation axis unit 230), the power consumption of the microscope device 10 can be reduced further, and the amount of heat produced in the support unit 120 can also be lowered.

Note that with regard to the arrangement of the actuators 320 and 330, in the first embodiment, the actuator 330 is provided as part of the third rotation axis unit 230 with respect to the third axis $O_2$. Meanwhile, as illustrated in the drawings, the actuator 320 is provided at a position distanced from the second rotation axis unit 220 with respect to the second axis $O_2$. Specifically, the second rotation axis unit 220 is arranged on the front end unit of the second arm unit 272, while the actuator 320 is arranged on the base end side of the second arm unit 272. Additionally, the second rotation axis unit 220 and the actuator 320 are connected by a power transmission mechanism (not illustrated) provided inside the second arm unit 272, and the driving force of the actuator 320 is transmitted to the second rotation axis unit 220 by the power transmission mechanism.

In the first embodiment, in this way, the second rotation axis unit 220 and the actuator 320 are arranged distanced from each other via the power transmission mechanism. According to this configuration, since the actuator 320 can be arranged at a position farther away from the second rotation axis unit 220 towards the base end side, the configuration near the second rotation axis unit 220, or in other words, the configuration near the microscope unit 110, can be miniaturized further. Consequently, it becomes possible to further secure the work space for the surgeon and the field of view for the surgeon described above. Note that the arrangement of the actuators 320 and 330 will be described in detail in conjunction with the description of the configuration of the manual brake mechanism in (1-3. Configuration of manual brake mechanism) below.

The above thus describes a configuration of the microscope system 1 and an overall configuration of the microscope device 10 according to the first embodiment, with reference to FIG. 1.

(1-2. Cases in which Picture of Operating Site is No Longer Displayed Normally)

As described above, in the microscope system 1, a picture of the operating site imaged by the microscope unit 110 is displayed on the display device 20. However, during an emergency such as a power failure, for example, or in a case in which a malfunction occurs in one of the devices constituting the microscope system 1, a situation is anticipated in which the picture of the operating site is no longer displayed normally on the display device 20.

In the microscope system 1, to further increase patient safety, it is desirable to be able to continue surgery, even in cases in which the picture of the operating site is no longer displayed normally for some reason. Note that conceivable reasons why the picture of the operating site is no longer display normally include a malfunction in the image sensor of the microscope unit 110, a malfunction in the display device 20, and/or a malfunction in the communication between the microscope device 10 and the display device 20.

Accordingly, in the first embodiment, in case in which the picture of the operating site is no longer display normally, there is provided an auxiliary observation device that is attachable to the microscope unit 110 or the support unit 120. The auxiliary observation device is a loupe, for example, and in the case in which the picture of the operating site is no longer displayed normally, the auxiliary observation device can be attached to the microscope unit 110 or the support unit 120, thereby enabling the surgeon to continue surgery while peering directly into the auxiliary observation device. Note that the storage location of the auxiliary observation device is not particularly limited, and the auxiliary observation device may be stored in a dedicated storage unit provided in the microscope device 10, or in an arbitrary location that is easily retrievable during an emergency, such as inside the operating room, for example.

A configuration of the auxiliary observation device will be described with reference to FIG. 2. FIG. 2 is a diagram illustrating a state in which an auxiliary observation device is attached to the first rotation axis unit 210. Note that FIG. 2 extracts only the microscope unit 110 and the first rotation axis unit 210 from the microscope device 10 illustrated in FIG. 1, and illustrates a state in which the auxiliary observation device is attached to these components. However, in FIG. 2, the configuration of the microscope unit 110 and the first rotation axis unit 210 is illustrated in greater detail than FIG. 1. Note that in FIG. 2, an exemplary configuration for the case in which the auxiliary observation device according to the first embodiment is a loupe is illustrated as an example. However, in the present disclosure, the auxiliary observation device is not limited to a loupe. It is sufficient for the auxiliary observation device to be provided with an optical system enabling enlarged observation of the operating site by having the surgeon peer directly into the device, and the specific configuration may be arbitrary.

As described in (1-1. Overall configuration of microscope device) above, the microscope unit 110 is made up of a barrel unit 112 having an approximately hollow round cylindrical shape, and an imaging unit provided inside the barrel unit 112. The first rotation axis unit 210 is connected to the base end unit of the barrel unit 112 of the microscope unit 110. At this point, part of the imaging unit of the microscope unit 110 is stored inside the hollow round cylindrical housing 211 constituting the first rotation axis unit 210. In other words, the microscope unit 110 and the first rotation axis unit 210 are configured as an integrated member. Note that since the imaging unit is provided inside the microscope unit 110 and the housing of the first rotation axis unit 210 in this way, in FIG. 2, illustration of the imaging unit is omitted to keep the drawings from becoming complicated.

The first rotation axis unit 210 rotatably supports the microscope unit 110 about the first axis $O_1$, and in this case, the housing 211 constituting the first rotation axis unit 210 is configured so that a section of a certain length from the bottom end of (hereinafter designated the rotating unit 212) rotates together with the microscope unit 110, while a section above the rotating unit 212 is a section that rotatably supports the microscope unit 110 and the rotating unit 212 about the first axis $O_1$ (hereinafter designated the fixed unit 213). The first arm unit 271 illustrated in FIG. 1 (not illustrated in FIG. 2) is connected to the fixed unit 213 of the first rotation axis unit 210. Also, part of the imaging unit of the microscope unit 110 may be stored inside the rotating unit 212 of the first rotation axis unit 210.

The auxiliary observation device 30 according to the first embodiment is made up of a lens barrel unit 301, an attachment mechanism unit 303, a connecting unit 305 that connects the lens barrel unit 301 and the attachment mechanism unit 303, and a securing member 307 for securing the auxiliary observation device 30 to the first rotation axis unit 210.

The lens barrel unit 301 is made up of a pair of lens barrels, inside of which is provided an optical system such as leases for performing enlarged observation of the operating site. Note that, for the sake of simplicity, the specific configuration is omitted from illustration, but the lens barrel unit 301 preferably is provided with an interpupillary adjustment mechanism enabling the distance between the lens barrels to be adjusted in accordance with the interpupillary distance of the surgeon. When using the auxiliary observation device 30, by appropriately adjusting the distance between the lens barrels with the interpupillary adjustment mechanism, the surgeon is able to observe the operating site more clearly.

The connecting unit 305 is a rod-shaped member, one end of which is connected to the lens barrel unit 301, while the other end is connected to the attachment mechanism unit 303.

The attachment mechanism unit 303 is a mechanism for attaching the auxiliary observation device 30 to the first rotation axis unit 210. In the illustrated example, the attachment mechanism unit 303 includes a first section made up of a planar member having an approximately semicircular shape corresponding to the circular shape of the top face of the housing 211 of the first rotation axis unit 210, and a second section made up of a planar member extending a certain length in an approximately perpendicular direction with respect to the top face of the housing 211 from the rim of the circular arc shape of the first section.

When the auxiliary observation device 30 is attached to the first rotation axis unit 210, the auxiliary observation device 30 is mounted onto the first rotation axis unit 210 so that the first section of the attachment mechanism unit 303 is placed on the top face of the housing 211 of the first rotation axis unit 210 (in other words, top face of the fixed unit 213), while the second section of the attachment mechanism unit 303 covers a region of a certain distance from the top face on the side face of the housing 211. In this way, in the illustrated embodiment, the auxiliary observation device 30 is attached to the fixed unit 213 of the first rotation axis unit 210.

The securing member 307 is a bolt, for example, and is a member for securing the auxiliary observation device 30 to the first rotation axis unit 210. Specifically, an opening is provided in a partial region of the second section of the attachment mechanism unit 303, and a screw thread is cut into the inner wall of the opening. As illustrated in FIG. 2, in the state in which the auxiliary observation device 30 is mounted onto the first rotation axis unit 210, by inserting and screwing the securing member 307 into the opening of the attachment mechanism unit 303 until the tip abuts the side wall of the housing 211 of the first rotation axis unit 210, the auxiliary observation device 30 is secured to the first rotation axis unit 210.

When the auxiliary observation device 30 is attached to the microscope unit 110, the connection angle of the lens barrel unit 301 of the auxiliary observation device 30 with respect to the connecting unit 305 (that is, the tilt angle with respect to the optical axis of the microscope unit 110), the optical system inside the lens barrel unit 301, and the like are adjusted to allow at least part of the observation range provided by the microscope unit 110 to be observed with the lens barrel unit 301. With this configuration, when the surgeon attaches the auxiliary observation device 30 and peers into the lens barrel unit 301 in a case in which the picture of the operating site is no longer displayed normally, the surgeon is able to observe a range corresponding to the range that had been imaged by the microscope unit 110 up until that time, and is able to continue surgery smoothly.

Herein, the connecting unit 305 is rotatably connected to the attachment mechanism unit 303. As illustrated in the drawing, for example, the rotation mechanism is realized by providing openings that penetrate through the connecting unit 305 and the attachment mechanism unit 303, and inserting a connecting member such as a bolt through these openings. The rotation axis of the connecting unit 305 is approximately parallel to the rotation axis in the first rotation axis unit 210 (first axis $O_1$).

As described above, in the illustrated example, the auxiliary observation device 30 is attached to the fixed unit 213 of the first rotation axis unit 210, and thus is unable to rotate together with the microscope unit 110. However, by providing a rotation mechanism as described above between the connecting unit 305 and the attachment mechanism unit 303, the lens barrel unit 301 can be rotated about the first axis $O_1$ with respect to the attachment mechanism unit 303, or in other words, with respect to the first rotation axis unit 210, making it possible to adjust the observation range provided by the auxiliary observation device 30.

The above thus describes a configuration of the auxiliary observation device with reference to FIG. 2. In the first embodiment, in the case in which the picture of the operating site is no longer displayed normally, the auxiliary observation device 30 is attached to the first rotation axis unit 210 as illustrated, thereby enabling the surgeon to observe the operating site directly through the lens barrel unit 301 by peering into the lens barrel unit 301 from the top part of the lens barrel unit 301. Consequently, until the state of the picture of the operating site not being displayed normally is resolved and the microscope system 1 is restored, the surgeon is able to continue surgery by using the auxiliary observation device 30, thereby making it possible to increase patient safety.

At this point, as the substitute means of observation in the case in which the picture of the operating site is no longer displayed normally, devices other than the auxiliary observation device 30, such as a head-mounted loupe worn on the surgeon's head, or another optical microscope device, for example, are conceivable. However, in the case of observing the operating site with a head-mounted loupe, to continue observing the operating site from a fixed position, it is necessary to keep constant the relative position of the surgeon's head with respect to operating site. Since the field of view of a loupe is limited, once the position of the head is moved, capturing the operating site in the field of observation again is not easy, and for a surgeon who is not particularly accustomed to using a head-mounted loupe, such a head-mounted loupe is not considered easy to use.

On the other hand, the case of using a substitute optical microscope device lead to increased cost equal to the cost of making available such a substitute microscope device. Also, since it is also necessary to prepare the substitute microscope device before surgery, the workload on the medical staff increases. Furthermore, since it is necessary to secure space to the install the substitute microscope device, the inside of the operating room becomes crowded.

In contrast, according to the first embodiment, as described above, the auxiliary observation device 30 is provided as a substitute means of observation in the case in which the picture of the operating site is no longer displayed normally. The auxiliary observation device 30 can be attached to the microscope unit 110 of the microscope device 10 with a simple operation, and the surgeon is able to continue observation of the operating site immediately using the auxiliary observation device 30.

At this point, in the case of using the auxiliary observation device 30, once the position of the microscope unit 110 has been set, the relative positional relationship of the operating site and the auxiliary observation device 30 can be locked, and thus even if the surgeon briefly moves his or her head away from the auxiliary observation device 30, the surgeon is able to observe the operating site again immediately by peering into the auxiliary observation device 30. Consequently, there is no nuisance like that of the head-mounted loupe described above. Also, the auxiliary observation device 30 can be made available at low cost compared to a substitute microscope device, and furthermore does not require advance preparation or the like. Additionally, the auxiliary observation device 30 may be configured compactly and a smaller space is sufficient as a storage location, and thus a situation in which the inside of the operating room becomes crowded can also be avoided.

In this way, by using the auxiliary observation device 30 as a substitute means of observation, it becomes possible to continue the observation of the operating site more easily compared to the case of using a head-mounted loupe or another optical microscope device.

Note that in the related art, there is known an endoscopic device in which, instead of the microscope unit 110, an endoscope is supported by the support unit 120 as illustrated in FIG. 1. Likewise with such an endoscopic device, similarly to the microscope device 10, it is desirable to be able to continue surgery even in the case in which the picture of the operating site is no longer displayed normally. However, although dependent on the site targeted for surgery and the surgical technique, in an endoscopic device, in the case in which the picture of the operating site is no longer displayed normally, there is a possibility that surgery can be continued by proceeding to abdominal or cranial surgery, for example. In other words, with an endoscopic device, in the case in which the picture of the operating site is no longer displayed normally, there is a possibility that surgery can be continued without necessarily using the auxiliary observation device 30.

On the other hand, with the microscope device 10, since a substitute means such as abdominal or cranial surgery for an endoscopic device does not exist, in the case in which the picture of the operating site is no longer displayed normally, surgery cannot be continued unless enlarged observation of the operating site is performed by some method. In this way, the auxiliary observation device 30 is considered to exhibit particularly advantageous effects by being used for a microscope device 10 in which abdominal or cranial surgery is presupposed.

Note that the configuration of the auxiliary observation device 30 illustrated in FIG. 2 and the method of attaching the auxiliary observation device 30 are merely one example. In the first embodiment, it is sufficient for the auxiliary observation device 30 to be attachable to any section of the microscope unit 110 or the support unit 120, and the configuration and attachment method thereof is not limited to the illustrated example. For example, the auxiliary observation device 30 may also be attached to the barrel unit 112 of the microscope unit 110, or to the rotating unit 212 of the housing 211 of the first rotation axis unit 210. In this case, the auxiliary observation device 30 is able to rotate about the first axis $O_1$ together with the microscope unit 110 and the rotating unit 212, and thus the auxiliary observation device 30 may also not be provided with a rotation mechanism as described above.

(1-3. Configuration of Manual Brake Mechanism)

Herein, as described in (1-1. Overall configuration of microscope device) above, in the microscope device 10, among the rotation axis units of the support unit 120, the second rotation axis unit 220 and the third rotation axis unit 230 are not provided with an electronically controlled brake mechanism, and rotation in these rotation axis units is driven by the actuators 320 and 330. This configuration makes it possible to achieve miniaturization of the configuration near the microscope unit 110, reduction in power consumption, and moderation of produced heat.

On the other hand, if the attachment of the auxiliary observation device 30 to the microscope device 10 is considered, since the support unit 120 of the microscope device 10 is configured as a balance arm, there is a risk that attaching the auxiliary observation device 30 may cause the balance to be lost, and cause the support unit 120 to be unable to maintain attitude. In this case, there is a possibility that the position of the auxiliary observation device 30 may not be secured, making it difficult to observe the operating site with the auxiliary observation device 30.

Such a phenomenon in which the support unit 120 cannot maintain attitude is thought to become an issue particularly in the case in which an electronically controlled brake mechanism is not provided in a subset of the rotation axis units, like with the support unit 120 of the microscope device 10. For example, consider a case in which in the case in which the picture of the operating site is no longer displayed normally, and the flow of current to the support unit 120 is also retarded or stopped. In this case, if all of the rotation axes constituting the support unit 120 are provided with electronically controlled brake mechanisms that engage in the absence of current, such as non-excitation (negative actuation) electromagnetic brakes, these electronically controlled brake mechanisms will engage, and the attitude of the support unit 120 can be maintained even if the auxiliary observation device 30 is attached to the support unit 120.

However, in the support unit 120 according to the first embodiment, electronically controlled brake mechanisms are not provided in the second rotation axis unit 220 and the third rotation axis unit 230, and the stopping of rotation in the second rotation axis unit 220 and the third rotation axis unit 230 is controlled by the actuators 320 and 330. In the absence of current, the actuators 320 and 330 cannot be driven, and thus rotation in the second rotation axis unit 220 and the third rotation axis unit 230 cannot be stopped adequately, and the attitude of the support unit 120 also changes to the extent that balance is lost due to the auxiliary observation device 30.

Note that since a motor typically has a holding torque, even in an absence of current, the motors provided in the actuators 320 and 330 are able to provide support if the torque is smaller than the holding torque. However, although dependent on the architecture of the actuators 320 and 330, the holding torque of the motors provided in the actuators 320 and 330 is not necessarily designed with additional consideration for the weight of the auxiliary observation device 30, and there is no guarantee that the weight of the auxiliary observation device 30 can be fully supported by the holding torque of the motors.

In this way, in the microscope device 10, since electronically controlled brake mechanisms are not provided in a subset of the rotation axis units of the support unit 120, a situation in which the attitude of the support unit 120 changes due to the attachment of the auxiliary observation device 30 in the case in which the picture of the operating site is no longer displayed normally is considered to occur more easily.

Accordingly, in the first embodiment, to maintain the attitude of the support unit 120, a manual brake mechanism for stopping rotation in the second rotation axis unit 220 and the third rotation axis unit 230 is provided. The manual brake mechanism is not used when operating the support unit 120 ordinarily, and is a brake that the surgeon operates manually only in the case of attaching the auxiliary observation device 30 in the case in which the picture of the operating site is no longer displayed normally.

In other words, in the first embodiment, in the case in which the picture of the operating site is no longer displayed normally, the surgeon attaches the auxiliary observation device 30 to the microscope unit 110 or the support unit 120. At this point, in cases in which a loss of power or the like has also occurred, and there is a risk of the actuators 320 and 330 being unable to operate normally, the surgeon additionally engages the above manual brake mechanism. By the manual brake mechanism, rotation is stopped in the second rotation axis unit 220 and the third rotation axis unit 230 not provided with an electronically controlled brake mechanism. Also, since the other rotation axis units (the first rotation axis unit 210, the fourth rotation axis unit 240, the fifth rotation axis unit 250, and the sixth rotation axis unit 260) are provided with electronically controlled brake mechanisms made up of non-excitation (negative actuation) electromagnetic brakes, for example, rotation in these rotation axis units can also be stopped by these electronically controlled brake mechanisms. Consequently, even in the case of attaching the auxiliary observation device 30 to the microscope unit 110 or the support unit 120 in the case in which the picture of the operating site is no longer displayed normally, the attitude of the support unit 120 can be maintained, making it possible to continue surgery more reliably.

Herein, even in cases in which electronically controlled brake mechanisms are provided in all of the rotation axis units constituting the support unit 120, if the braking force is small, there is a possibility that attaching the auxiliary observation device 30 may cause the support unit 120 to be unable to maintain attitude. Meanwhile, even in cases in which electronically controlled brake mechanisms are not provided in a subset of the rotation axis units constituting the support unit 120 and the stopping of rotation is controlled by actuators, like in the first embodiment, if the holding torque of the motors in the actuators is sufficiently large, there is a possibility that the attitude of the support unit 120 may be maintained even if the auxiliary observation device 30 is attached.

In the first embodiment, as an example, a manual brake mechanism is provided with respect to the second rotation axis unit 220 and the third rotation axis unit 230 which are considered to have a small holding torque and a small braking force, but the present disclosure is not limited to such an example. By considering the braking force in each rotation axis unit constituting the support unit 120, the manual brake mechanism may be provided favorably with respect to a rotation axis unit having a smaller braking force, for which there is a possibility of the attitude of the support unit 120 changing in the case of attaching the auxiliary observation device 30.

Figure 3:
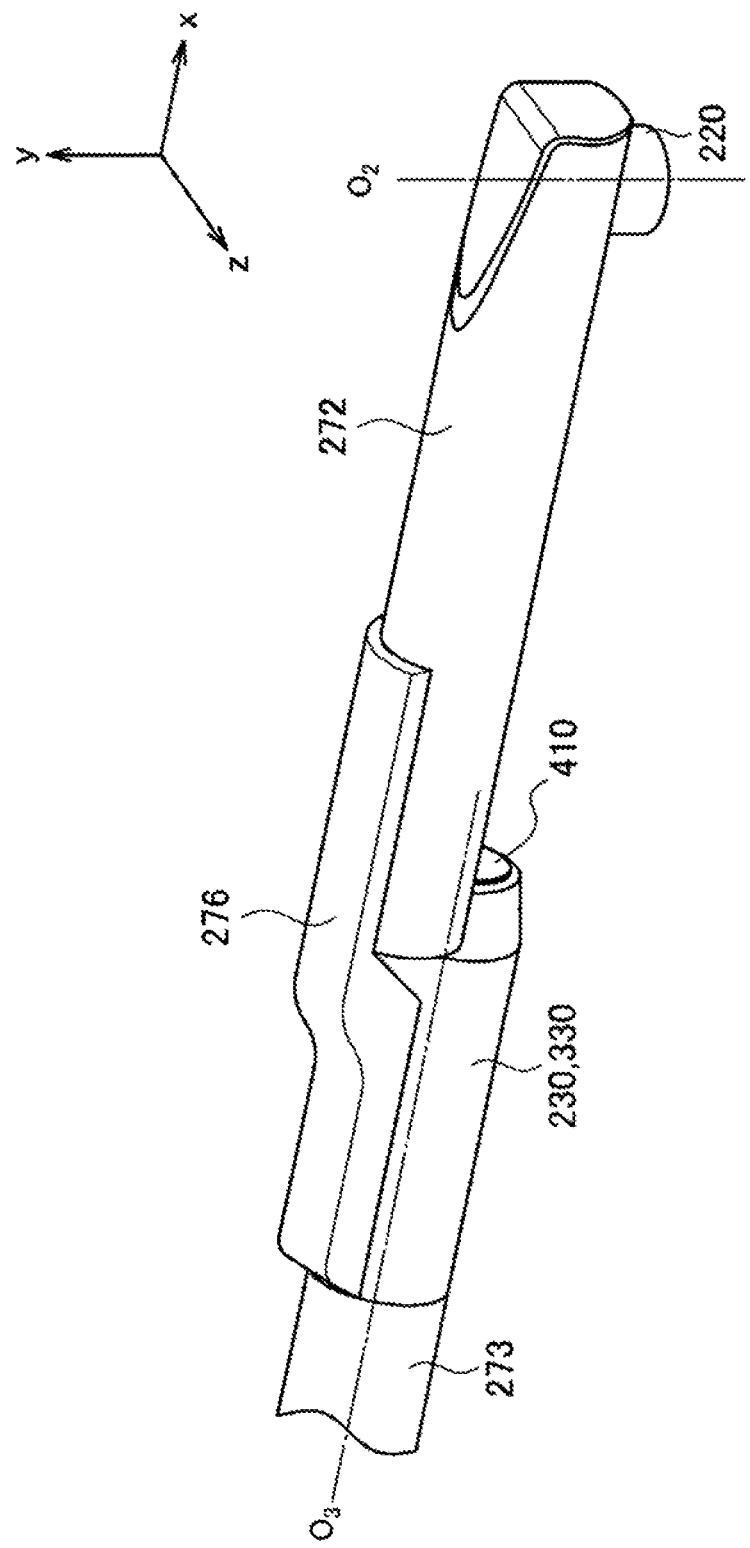
FIG. 3 is an exterior view illustrating the configuration of a section corresponding to a second arm unit, a third rotation axis unit, and a third arm unit of a support unit in a first embodiment.
Figure 4:
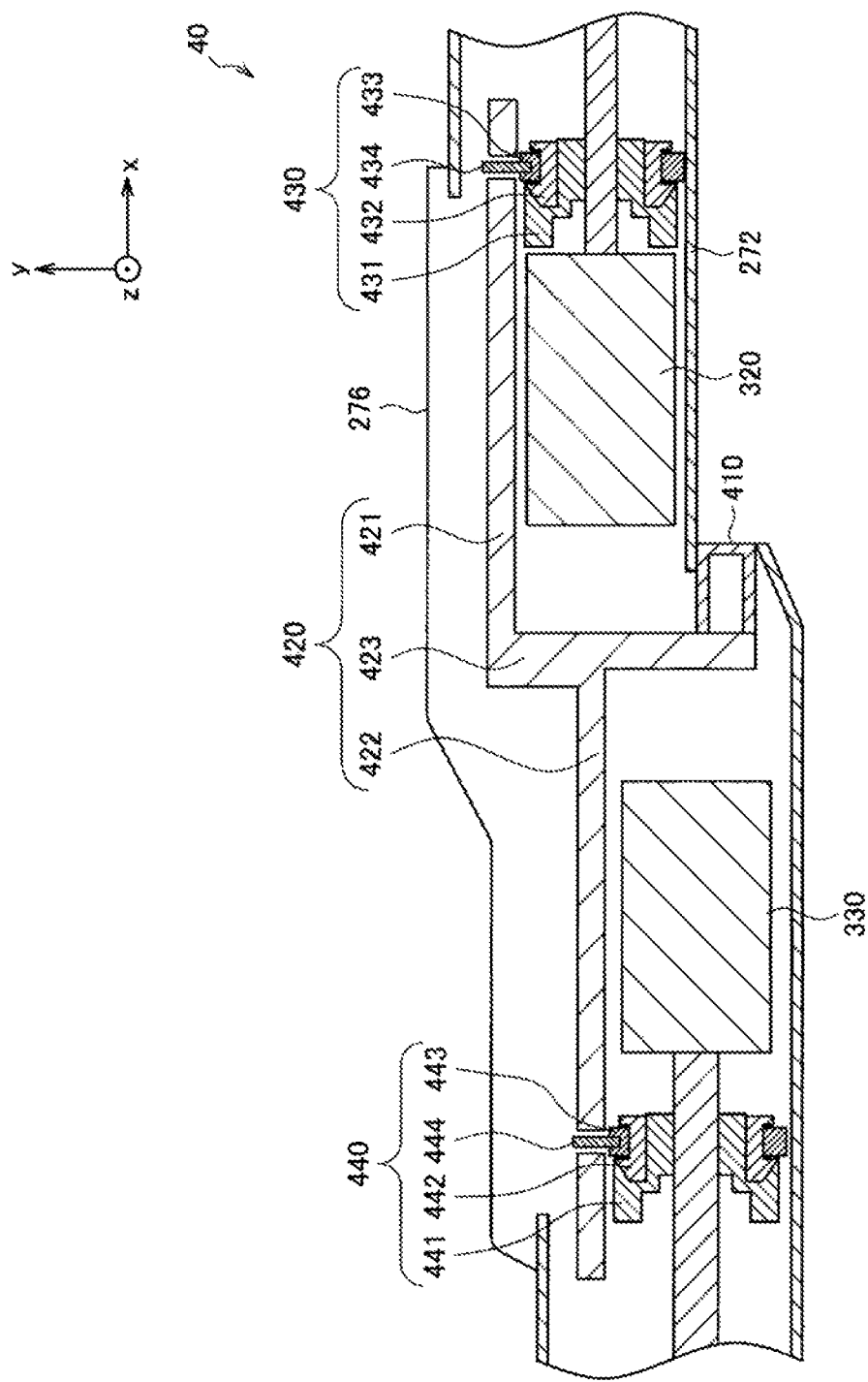
FIG. 4 is a cross-section diagram of a section corresponding to a manual brake mechanism in the second arm unit, the third rotation axis unit, and the third arm unit illustrated in FIG. 3.

Hereinafter, the configuration of a manual brake mechanism according to the first embodiment will be described in further detail with reference to FIGS. 3 and 4. FIG. 3 is an exterior view illustrating the configuration of a section corresponding to the second arm unit 272, the third rotation axis unit 230, and the third arm unit 273 of the support unit 120 in the first embodiment. FIG. 4 is a cross-section diagram of a section corresponding to a manual brake mechanism in the second arm unit 272, the third rotation axis unit 230, and the third arm unit 273 illustrated in FIG. 3. FIG. 3 illustrates an extraction of the second arm unit 272, the third rotation axis unit 230, and the third arm unit 273 from the configuration of the support unit 120 illustrated in FIG. 1. Also, FIG. 4 is a cross-section diagram along a cross-section parallel to the extension direction of the second arm unit 272, the third rotation axis unit 230, and the third arm unit 273 illustrated in FIG. 3. In FIG. 4, the illustration of the configuration near the actuators 320 and 330 is enlarged to explain the configuration of the manual brake mechanism.

In the first embodiment, a manual brake mechanism 40 stops rotation in the second rotation axis unit 220 and the third rotation axis unit 230 by applying brakes to the rotation of the drive shafts of the actuators 320 and 330. Accordingly, before describing the configuration of the manual brake mechanism 40, first, the configuration of the second arm unit 272, the third rotation axis unit 230, and the third arm unit 273 will be described in further detail, and the placement of the actuators 320 and 330 inside this configuration will be described.

Referring to FIG. 3, the second rotation axis unit 220 is connected to the front end of the second arm unit 272 having an approximately hollow round cylindrical shape, while the base end side thereof is connected to the third rotation axis unit 230 having the same approximately hollow round cylindrical shape. The direction of the rotation axis in the second rotation axis unit 220 (the second axis $O_2$) is a direction which is approximately perpendicular to the extension direction of the second arm unit 272. Also, the direction of the rotation axis in the third rotation axis unit 230 (the third axis $O_3$) is a direction which is approximately parallel to the extension direction of the second arm unit 272. Furthermore, the front end of the third arm unit 273 is connected to the base end of the third rotation axis unit 230. The extension direction of the third arm unit 273 is a direction approximately parallel to the third axis $O_3$ direction.

Herein, the second arm unit 272 and the third rotation axis unit 230 are connected in a state whereby the central axes are offset by a certain distance. In other words, the second arm unit 272 and the third rotation axis unit 230 are connected to constitute what is called a crank shape.

Although omitted from illustration in FIG. 1, the second arm unit 272 and the third rotation axis unit 230 are provided with a cover member 276 that extends in the same direction as the extension direction of the second arm unit 272 and the third rotation axis unit 230, so as to cover the crank part. The second arm unit 272 and the third rotation axis unit 230 are provided with an opening for disposing various members internally in a partial region of the partition of the housing, and the cover member 276 may be disposed to cover this opening.

As described above in (1-1. Overall configuration of microscope device), the actuator 330 that rotationally drives the second arm unit 272 about the third axis $O_2$ is provided inside the third rotation axis unit 230. Meanwhile, the actuator 320 that rotationally drives the first arm unit 271 (not illustrated in FIG. 3) about the second axis $O_2$ is disposed at a position distanced from the second rotation axis unit 220. Specifically, the actuator 320 is provided on the base end side of the second arm unit 272, and the driving force of the actuator 320 is transmitted to the second rotation axis unit 220 by a power transmission mechanism provided inside the second arm unit 272. Consequently, in the first embodiment, as illustrated in FIG. 4, the actuators 320 and 330 are disposed at positions close to each other.

As illustrated in FIG. 4, the actuator 320 is disposed inside the second arm unit 272 so that the rotation axis direction of the drive shaft is approximately parallel to the extension direction of the second arm unit 272. The power transmission mechanism is made up of a shaft, which is disposed inside the second arm unit 272 along the extension direction of the second arm unit 272 with the base end connected to the drive shaft of the actuator 320, and which rotates coaxially with the drive shaft, a first bevel gear provided on the front end of the shaft, and a second bevel gear that engages with the first bevel gear and rotates coaxially with the second rotation axis unit 220, for example. However, the configuration of the power transmission mechanism is not limited to such an example, and the power transmission mechanism may also be configuration by an appropriate combination of any of various mechanisms typically used when transmitting motive power, such as belts, pulleys, and gears, for example.

Note that by distancing the actuator 320 and the second rotation axis unit 220 from each other, the actuator 320 can be arranged at a position farther away from the second rotation axis unit 220 towards the base end side, and thus the configuration near the second rotation axis unit 220, or in other words, the configuration near the microscope unit 110, can be miniaturized further. Consequently, it becomes possible to further secure the work space for the surgeon and the field of view for the surgeon.

Also, in the illustrated configuration, the actuator 320 and the second rotation axis unit 220 are disposed so that the rotation axis direction of the drive shaft of the actuator 320 and the direction of the rotation axis of the second rotation axis unit 220 (the second axis $O_2$) are approximately orthogonal to each other. In other words, the actuator 320 is disposed so that the drive shaft faces in a direction approximately parallel to the extension direction of the second arm unit 272. Consequently, the amount by which the actuator 320 projects in a direction approximately orthogonal to the extension direction of the second arm unit 272 can be reduced. If a section that projects greatly in a direction approximately orthogonal to the extension direction of the second arm unit 272 exists, the projecting section projects towards the surgeon's body, and thus poses a risk of becoming an impediment to the surgeon's work during surgery. According to the illustrated configuration, the amount by which the projecting section projects can be reduced, thereby further improving workability for the surgeon.

Next, a configuration of the manual brake mechanism 40 according to the first embodiment will be described with reference to FIG. 4. Referring to FIG. 4, the manual brake mechanism 40 is made up of a switch 410, a cam slider 420 that operates in conjunction with the switch 410, a first cone brake 430 attached to the drive shaft of the actuator 320, and a second cone brake 440 attached to the drive shaft of the actuator 330.

Pressing the switch 410 causes the cam slider 420 to move in the direction of the press (in the diagram, the negative x-axis direction). In conjunction with the cam slider 420, a movable part of the first cone brake 430 and a movable part of the second cone brake 440 move to be pressed against a stationary part of the first cone brake 430 and a stationary part of the second cone brake 440, respectively, and a brake is applied to the rotation of the drive shafts of the actuator 320 and the actuator 330 (that is, the rotation of the second rotation axis unit 220 and the third rotation axis unit 230). In this way, in the first embodiment, a single action of pressing the switch 410 by the surgeon can cause a brake to be applied to both the second rotation axis unit 220 and the third rotation axis unit 230. Note that FIG. 4 illustrates the state when the switch 410 is pressed, and the first cone brake 430 and the second cone brake 440 of the manual brake mechanism 40 are applied.

The configuration of the manual brake mechanism 40 will be described in further detail. As illustrated in FIG. 4, the switch 410 is provided in the crank part, namely the connecting part between the second arm unit 272 and the third rotation axis unit 230. The switch 410 has an approximately hollow round cylindrical shape, with one end exposed to the outside, and the other end positioned inside the housing of the second arm unit 272 and the third rotation axis unit 230. The switch 410 is configured to be movable in the extension direction of the second arm unit 272 and the third rotation axis unit 230. Pressing the one end of the switch 410 that is exposed to the outside causes the other end of the switch 410 to press against the cam slider 420, which causes the cam slider 420 to move in the pressed direction (in the diagram, the negative x-axis direction).

Herein, the switch 410 may be provided with what is called a nock cam mechanism (not illustrated). By providing a nock cam mechanism, once the switch 410 is pressed, the switch 410 is secured at the pressed position, thereby causing the first cone brake 430 and the second cone brake 440 to enter a continuously engaged state. In the case of wanting to release the first cone brake 430 and the second cone brake 440, it is sufficient to press the switch 410 again. Note to prevent malfunction of the manual brake mechanism 40, a configuration such as a stopper (not illustrated) that impedes smooth movement of the switch 410 may be provided appropriately so that the switch 410 moves only when pressed with a force of at least a certain magnitude.

The cam slider 420 is disposed inside the housing of the second arm unit 272 and the third rotation axis unit 230. The cam slider 420 configured by the integral connection of a planar first member 421 running along the second arm unit 272, a planar second member 422 running along the third rotation axis unit 230, and a planar third member 423 which joins the first member 421 and the second member 422 and which runs in a direction approximately perpendicular to the extension direction of the second arm unit 272 and the third rotation axis unit 230. The third member 423 is disposed so that the planar face opposes the other end of the switch 410. By pressing the switch 410, the planar face of the third member 423 is pressed by the switch 410, and the entire cam slider 420 moves in the pressed direction.

The first cone brake 430 and the second cone brake 440 are friction brakes that produce braking force due to fiction at a contact surface caused by the conical surface of a movable part being pressed against the conical surface of a stationary part. Note that in the illustrated exemplary configuration, to improve the frictional force, a cone brake in which the friction surface is a conical surface is used, but as long as the desired frictional force is obtained, a disc brake in which the movable part and the stationary part are disc-shaped and the contact surface is a flat plane may also be used.

In the illustrated exemplary configuration, the first cone brake 430 is made up of a stationary part 431, a first movable part 432, and a second movable pan 433. The stationary part 431, the first movable part 432, and the second movable part 433 are all ring-shaped, and are attached to the drive shaft of the actuator 320 so as to overlap each other in the above order as viewed from the actuator 320 in the direction of the drive shaft.

The stationary part 431 is securely fitted onto the drive shaft of the actuator 320, and rotates together with the drive shaft of the actuator 320 in association with the driving of the actuator 320. The face of the stationary part 431 that opposes the first movable part 432 has a conical shape.

The first movable part 432 is attached to the drive shaft of the actuator 320 so as to be movable in the direction of the drive shaft, and the face that opposes the stationary part 431 has a conical shape corresponding to the conical shape of the 80 stationary part 431. By causing the first movable part 432 to move in the direction of the stationary part 431 and the conical surface of the first movable part 432 to be pressed against the conical surface of the stationary part 431, the rotation of the stationary part 431, or in other words the rotation of the drive shaft of the actuator 320, is stopped.

The second movable part 433 is attached on the opposite side of the stationary part 431 with the first movable part 432 interposed between on the drive shaft of the actuator 320, so as to be movable in the direction of the drive shaft of the actuator 320. Also, the outer circumference of the ring shape of the second movable part 433 is provided with a pin 434 that projects in a direction perpendicular to the extension direction of the second arm unit 272.

On the first member 421 of the cam slider 420, an opening is provided at a position corresponding to the pin 434 provided on the second movable part 433, with the cam slider 420 and the first cone brake 430 being disposed so that the pin 434 is inserted into this opening. The opening is formed to extend in a direction tilted by a certain angle from a direction perpendicular to the extension direction of the first member 421 (in the drawing, the z-axis direction). If the cam slider 420 moves in the x-axis direction of the drawing while in the state in which the pin 434 is fitted into the opening, the pin 434 moves along the extension direction of the opening, and correspondingly, the second movable part 433 joined to the pin 434 moves along the drive shaft of the actuator 320 while also rotating about the drive shaft.

In other words, in the illustrated configuration, by causing the switch 410 to be pressed in the negative x-axis direction of the drawing, and correspondingly causing the first member 421 of the cam slider 420 to move in the negative x-axis direction, the second movable part 433 also moves in the negative x-axis direction via the pin 434. A flat spring (not illustrated) is provided between the opposing faces in the x-axis direction of the second movable part 433 and the first movable part 432, so that by causing the second movable part 433 to move in the negative x-axis direction, the first movable part 432 is pressed in the negative x-axis direction by the second movable part 433 through the flat spring. Subsequently, the conical surface of the first movable part 432 is pressed against the conical surface of the stationary part 431, and the first cone brake 430 is engaged.

The configuration and operation of the second cone brake 440 are mostly similar to the first cone brake 430. However, given the relationship of the cam slider 420 with respect to the movement direction, the direction in which the second cone brake 440 is attached to the actuator 330 is the opposite of the first cone brake 430.

Specifically, the second cone brake 440 is made up of a stationary part 441, a first movable part 442, and a second movable part 443. The second movable part 443, the first movable part 442, and the stationary part 441 are all ring-shaped, and are attached to the drive shaft of the actuator 330 so as to overlap each other in the above order as viewed from the actuator 330 in the direction of the drive shaft.

The stationary part 441 is securely fitted onto the drive shaft of the actuator 330, and rotates together with the drive shaft of the actuator 330 in association with the driving of the actuator 330. The first movable part 442 is attached to the drive shaft of the actuator 330 so as to be movable in the direction of the drive shaft. The opposing faces of the stationary part 441 and the second member 422 are both conical surfaces, and by causing the first movable part 442 to move in the direction of the stationary part 441 and the conical surface of the first movable part 442 to be pressed against the conical surface of the stationary part 441, the rotation of the stationary part 441, or in other words the rotation of the drive shaft of the actuator 330, is stopped.

The second movable part 443 is attached on the opposite side of the stationary part 441 with the first movable part 442 interposed between on the drive shaft of the actuator 330, so as to be movable in the direction of the drive shaft of the actuator 330. Also, the outer circumference of the ring shape of the second movable part 443 is provided with a pin 444 that projects in a direction perpendicular to the extension direction of the second arm unit 272.

On the second member 422 of the cam slider 420, an opening is provided at a position corresponding to the pin 444 provided on the second movable part 443, with the cam slider 420 and the second cone brake 440 being disposed so that the pin 444 is inserted into this opening. The opening is formed to extend in a direction tilted by a certain angle from a direction perpendicular to the extension direction of the second member 422 (in the drawing, the z-axis direction). If the cam slider 420 moves in the x-axis direction of the drawing while in the state in which the pin 444 is fitted into the opening, the pin 444 moves along the extension direction of the opening, and correspondingly, the second movable part 443 joined to the pin 444 moves along the drive shaft of the actuator 330 while also rotating about the drive shaft.

In other words, in the illustrated configuration, by causing the switch 410 to be pressed in the negative x-axis direction of the drawing, and correspondingly causing the second member 422 of the cam slider 420 to move in the negative x-axis direction, the second movable part 443 also moves in the negative x-axis direction via the pin 444. A flat spring (not illustrated) is provided between the opposing faces in the x-axis direction of the second movable part 443 and the first movable part 442, so that by causing the second movable part 443 to move in the negative x-axis direction, the first movable part 442 is pressed in the negative x-axis direction by the second movable part 443 through the flat spring. Subsequently, the conical surface of the first movable part 442 is pressed against the conical surface of the stationary part 441, and the second cone brake 440 is engaged.

The above thus describes a configuration of the manual brake mechanism 40 according to the first embodiment with reference to FIG. 3 and FIG. 4. Herein, the case in which the manual brake mechanism 40 is actually used, or in other words, the case in which the picture of the operating site is no longer displayed normally, is an emergency, and thus it is not preferable to impose a complicated operation on the surgeon as the operation for engaging the manual brake mechanism 40. It is desirable to engage the manual brake mechanism 40 and cause the attitude of the support unit 120 to be locked with a simpler operation. Meanwhile, as described above, according to the first embodiment, there is provided a manual brake mechanism 40 capable of applying brakes to multiple rotation axis units at the same time. According to the manual brake mechanism 40, the surgeon is able to apply brakes to multiple rotation axis units at the same time with a single and comparatively simple operation of pressing the switch 410. Consequently, it becomes possible to maintain the attitude of the support unit 120 more rapidly and continue surgery, without imposing an excessive burden on the surgeon.

Note that the microscope device 10 may be favorably provided with a detection mechanism that detects whether the manual brake mechanism 40 has been engaged. Additionally, in the case in which the detection mechanism detects that the manual brake mechanism 40 has been engaged, driving control of the actuators 320 and 330 by the control device 140 may be stopped.

In the case in which the picture of the operating site is no longer displayed normally, it is difficult for the surgeon to ascertain the cause immediately. Consequently, a situation may be anticipated in which, in order to continue surgery as quickly as possible, the surgeon attaches the auxiliary observation device 30 and activates the manual brake mechanism 40, regardless of the cause by which the picture of the operating site is no longer displayed normally. If the rotation of the drive shafts of the actuators 320 and 330 is stopped forcibly with the manual brake mechanism 40 even though the driving control of the actuators 320 and 330 by the control device 140 is still being conducted normally, there is a risk that the control of the actuators 320 and 330 may become unstable, and the support unit 120 may move unexpectedly.

Consequently, as described above, by stopping the driving control of the actuators 320 and 330 by the control device 140 in the case of detecting that the manual brake mechanism 40 has been engaged, it becomes possible to avoid a situation in which the support unit 120 moves unexpectedly, and lock the attitude of the support unit 120 more reliably.

Note that a manual describing information such as how to attach and how to use the auxiliary observation device 30 as well as how to use the manual brake mechanism 40 may also be kept together with the auxiliary observation device 30 in the storage location of the auxiliary observation device 30. Such a manual additionally may explain how the driving control of the actuators 320 and 330 by the control device 140 is stopped in the case of engaging the manual brake mechanism as described above. Since each of the auxiliary observation device 30 and the manual brake mechanism 40 is a device which may be used only during an emergency in the case in which the picture of the operating site is no longer displayed normally, ordinarily, it is anticipated that the surgeon will not have a firm grasp on how to use the auxiliary observation device 310. In this way, keeping a manual in a location allowing easy reference by the surgeon is considered to be extremely useful to the surgeon.

Note that the configuration illustrated in FIGS. 3 and 4 is merely one example, and the first embodiment is not limited to such an example. In the first embodiment, it is sufficient to configure a manual brake mechanism that acts at the same time on multiple rotation axis units (in the illustrated example, the second rotation axis unit 220 and the third rotation axis unit 230) considered to have insufficient braking force to maintain the attitude of the support unit 120, and the specific configuration may be designed appropriately.

2. Second Embodiment

As described above, in the first embodiment, there is proposed a manual brake mechanism 40 capable of applying brakes to both the second rotation axis unit 220 and the third rotation axis unit 230 with a single operation of pressing the switch 410 by the surgeon.

However, depending on the configuration of the support unit 120, the manual brake mechanism 40 that applies brakes to two rotation axis units at the same time with a single operation like in the first embodiment may not necessarily be realizable.

For example, in the exemplary configuration illustrated in FIGS. 3 and 4, since the actuator 320 and the second rotation axis unit 220 are arranged distanced from each other via the power transmission mechanism, as a result, the two actuators 320 and 330 corresponding to the two rotation axis units (the second rotation axis unit 220 and the third rotation axis unit 230) are arranged at positions comparatively close to each other. Consequently, the manual brake mechanism 40 that acts at the same time on the drive shafts of the actuators 320 and 330 with a single operation as described above can be realized with a comparatively simple configuration.

However, for multiple actuators arranged at comparatively distant positions from each other, realizing a manual brake mechanism that acts at the same time on the drive shafts of these multiple actuators is considered to be more difficult. In this case, it is more realistic to provide each actuator with a manual brake mechanism individually.

In addition, to maintain the attitude of the support unit 120, it is not strictly necessary to provide a manual brake mechanism with respect to multiple rotation axis units. For example, as a result of thorough investigation, the inventors have found that even with a support unit 120 having a configuration similar to the configuration illustrated in FIG. 1 (that is, even with a configuration in which the second rotation axis unit 220 and the third rotation axis unit 230 are not provided with electronically controlled brake mechanisms, but are provided with the actuators 320 and 330), by making innovations to features such as the arrangement and shape of each arm unit and each rotation axis unit, when the auxiliary observation device is attached, the attitude of the support unit 120 may be maintained without providing the second rotation axis unit 220 with a manual brake mechanism. In this way, depending on the configuration of the support unit 120, cases are possible in which it is sufficient to provide a manual brake mechanism in only one rotation axis unit (in this case, the third rotation axis unit 230).

Note that in the above example, the statement that the attitude of the support unit 120 may be maintained without providing the second rotation axis unit 220 with a manual brake mechanism means that, to maintain the attitude of the support unit 120, it is considered sufficient for each rotation axis unit to have a holding force (braking force) that is enough to support the rotation moment corresponding to the configuration provided farther on the front end than the relevant rotation axis unit. For this reason, the farther on the base end side that a rotation axis unit is provided, a greater holding force (braking force) becomes required. In other words, if given the example described above, the components provided farther on the front end side than the second rotation axis unit 220 are fewer, more lightweight, and shorter in length than the components provided farther on the front end side than the third rotation axis unit 230, and thus in the second rotation axis unit 220, the components provided farther on the front end side than the second rotation axis unit 220 can be supported by just the holding force of the actuator 320, and the attitude of the support unit 120 is maintained even without providing a manual brake mechanism.

In this way, depending on the configuration of the support unit 120, in some cases it is preferable to provide a manual brake mechanism that acts on only one rotation axis unit. In correspondence with such cases, the second embodiment proposes a manual brake mechanism that acts on one rotation axis unit.

Note that the second embodiment corresponds to a modification of the configuration of the manual brake mechanism with respect to the first embodiment described above, and other features (such as the configuration of the microscope system 1 and the overall configuration of the microscope device 10, for example) are similar to the first embodiment. Consequently, in the following description of the second embodiment, the features that differ from the first embodiment will be described primarily, whereas detailed description of features that overlap with the first embodiment will be reduced or omitted.

(2-1. Configuration of Manual Brake Mechanism)

A configuration of a manual brake mechanism according to the second embodiment will be described with reference to FIGS. 5 to 7. Note that as an example, the second embodiment describes a case in which, with respect to the configuration of the support unit 120 illustrated in FIG. 1, the third rotation axis unit 230 is provided with a manual brake mechanism. Specifically, the manual brake mechanism according to the second embodiment applies a brake to rotation of the drive shaft of the actuator 330 corresponding to the third rotation axis unit 230, and thereby stops the rotation in the third rotation axis unit 230.

Figure 5:
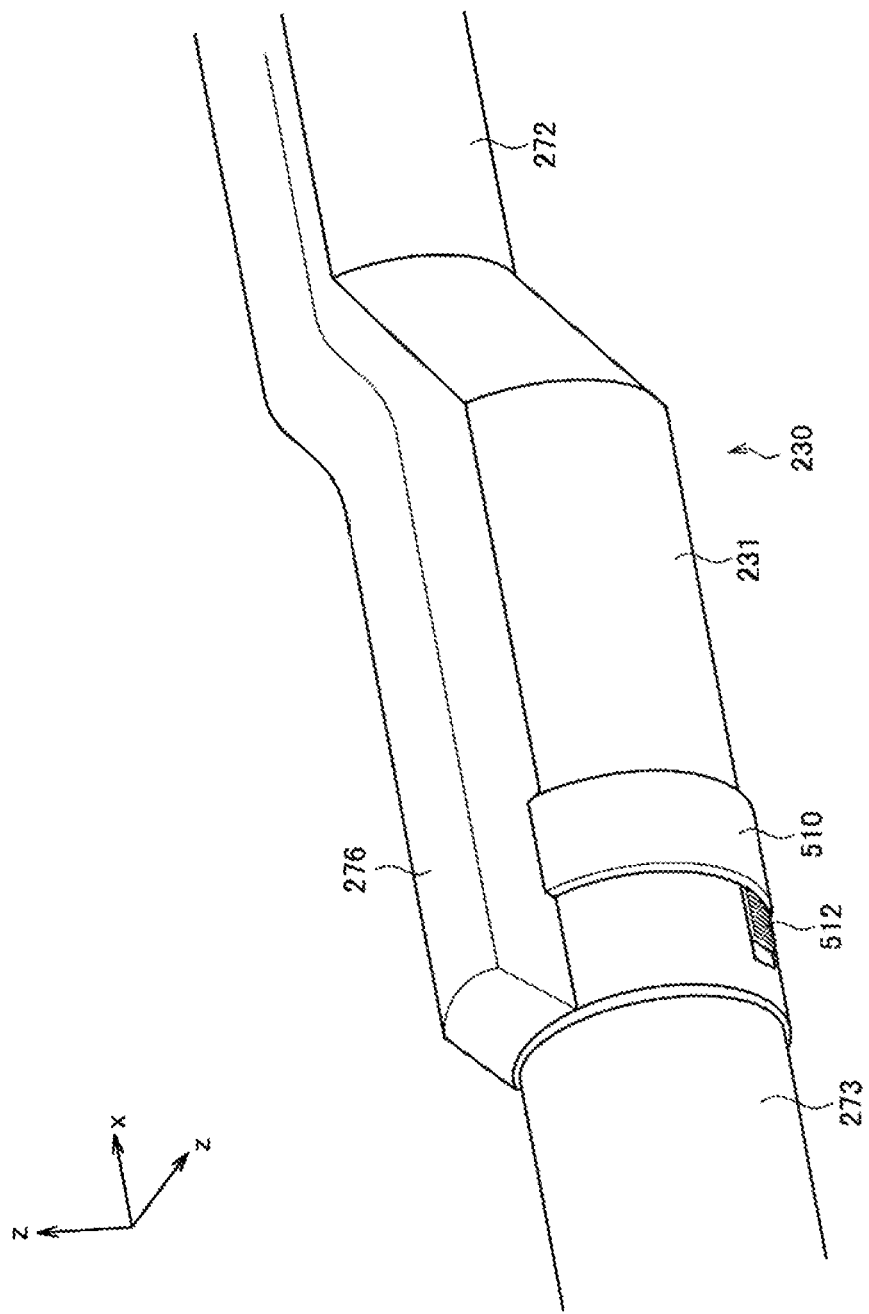
FIG. 5 is an exterior view illustrating the configuration of a section corresponding to a second arm unit, a third rotation axis unit, and a third arm unit of a support unit in a second embodiment.

FIG. 5 is an exterior view illustrating the configuration of a section corresponding to the second arm unit 272, the third rotation axis unit 230, and the third arm unit 273 of the support unit 120 in the second embodiment. FIG. 6 is an exterior view illustrating a state in which the cover member 276 has been removed from the configuration illustrated in FIG. 5. FIG. 7 is a cross-section diagram of a section corresponding to a manual brake mechanism in the second arm unit 272, the third rotation axis unit 230, and the third arm unit 273 illustrated in FIG. 5.

FIG. 5 illustrates an extraction of the second arm unit 272, the third rotation axis unit 230, and the third arm unit 273 from the configuration of the support unit 120 illustrated in FIG. 1. Also, FIG. 6 illustrates an internal configuration when the cover member 276 illustrated in FIG. 5 is removed, as viewed from the opening that had been covered by the cover member 276. Also, FIG. 7 is a cross-section diagram along a cross-section parallel to the extension direction of the second arm unit 272, the third rotation axis unit 230, and the third arm unit 273 illustrated in FIG. 5. In FIG. 7, the illustration of the configuration near the actuator 330 is enlarged to explain the configuration of the manual brake mechanism.

Since the general configuration of the second arm unit 272, the third rotation axis unit 230, and the third arm unit 273 (such as the connection relationships among the second arm unit 272, the third rotation axis unit 230, and the third arm unit 273, as well as the arrangement of the actuators 320 and 330) has already been described with reference to FIG. 3, detailed description thereof will be reduced or omitted herein. However, in the second embodiment, the configuration of the manual brake mechanism is different from the first embodiment. Consequently, in the configuration illustrated in FIG. 5, the switch 410 which is a component member of the manual brake mechanism 40 according to the first embodiment is not provided, and instead, a ring-shaped switch 510 which is a component member of the manual brake mechanism 50 according to the second embodiment is provided.

Figure 6:
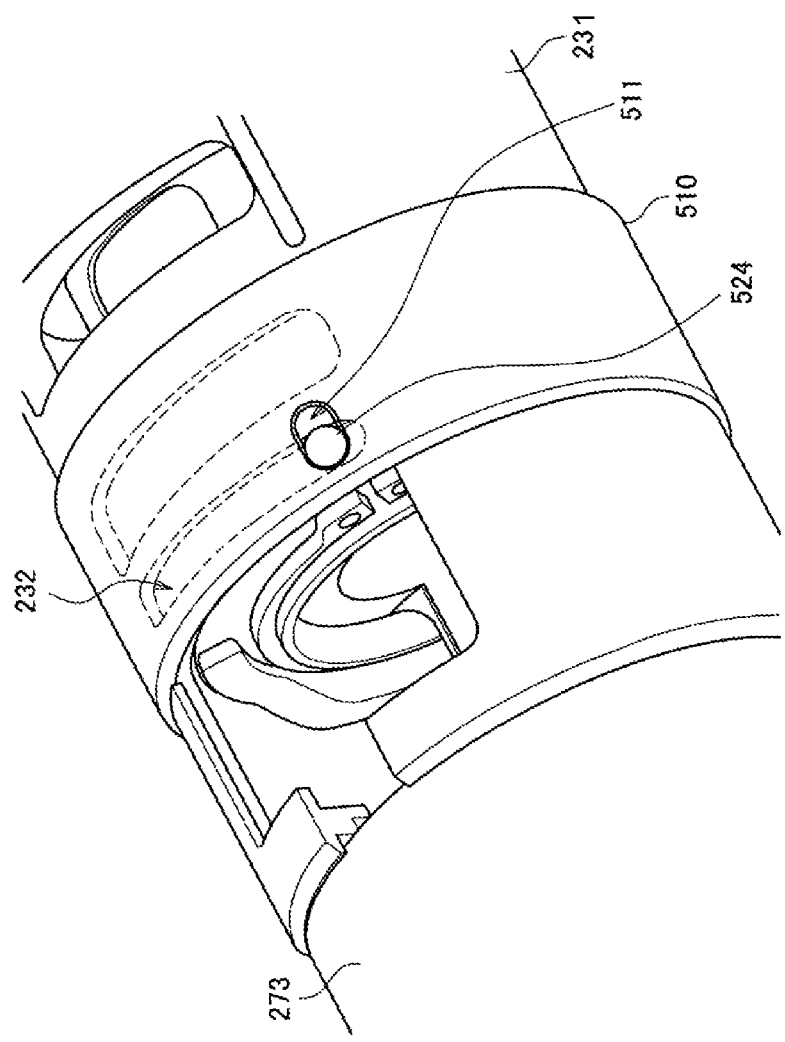
FIG. 6 is an exterior view illustrating a state in which a cover member has been removed from the configuration illustrated in FIG. 5.

Referring to FIGS. 5 to 7, the manual brake mechanism 50 according to the second embodiment is made up of the ring-shaped switch 510, and a cone brake 520 attached to the drive shaft of the actuator 330.

The ring-shaped switch 510 is provided in a partial region in the extension direction of the third rotation axis unit 230, and in a band shape so as to cover the outer circumference of a hollow round cylindrical housing 231 of the third rotation axis unit 230. The ring-shaped switch 510 is configured to be rotatable along the outer circumference of the housing 231.

The cone brake 520 is a friction brake that produces braking force due to fiction at a contact surface caused by the conical surface of a movable part being pressed against the conical surface of a solid part. Note that in the illustrated exemplary configuration, to improve the frictional force, a cone brake in which the friction surface is a conical surface is used, but as long as the desired frictional force is obtained, a disc brake in which the movable part and the stationary part are disc-shaped and the contact surface is a flat plane may also be used.

In the illustrated exemplary configuration, the cone brake 520 is made up of a stationary part 521, a first movable part 522, and a second movable part 523. The stationary pan 521, the first movable part 522, and the second movable part 523 are all ring-shaped, and are attached to the outer circumference of the actuator 330 so as to overlap each other in the above order as viewed from the actuator 330 in the direction of the drive shaft of the actuator 330.

The stationary part 521 is securely connected to the drive shaft (not illustrated) of the actuator 330, and rotates together with the drive shaft of the actuator 330 in association with the driving of the actuator 330. The face of the stationary part 521 that opposes the first movable part 522 has a conical shape.

The first movable part 522 is attached to the outer circumference of the actuator 330 so as to be movable in the direction of the drive shaft of the actuator 330, and the face that opposes the stationary part 521 has a conical shape corresponding to the conical shape of the stationary part 521. By causing the first movable part 522 to move in the direction of the stationary part 521 and the conical surface of the first movable part 522 to be pressed against the conical surface of the stationary part 521, the rotation of the stationary part 521, or in other words the rotation of the drive shaft of the actuator 330, is stopped.

The second movable part 523 is attached on the opposite side of the stationary part 521 with the first movable part 522 interposed between on the outer circumference of the actuator 330, so as to be movable in the direction of the drive shaft of the actuator 330. Also, the outer circumference of the ring shape of the second movable part 523 is provided with a projecting part 524 that projects in a direction perpendicular to the extension direction of the third rotation axis unit 230 (in other words, the rotation axis direction of the drive shaft of the actuator 330).

Herein, as illustrated in FIG. 6, an opening 511 is provided in a partial region of the ring-shaped switch 510. Also, the housing 231 of the third rotation axis unit 230 is provided with an opening 232 that extends in a direction tilted by a certain angle from the outer circumferential direction. The opening 511 and the opening 232 are provided so that partial regions thereof overlap each other.

The projecting part 524 of the second movable part 523 of the cone brake 520, the opening 232, and the opening 511 are formed so that the projecting part 524 is inserted into both the opening 232 of the housing 231 of the third rotation axis unit 230 and the opening 511 of the ring-shaped switch 510.

As described above, the opening 232 is formed to extend in a direction tilted by a certain angle from the outer circumferential direction of the housing 231 of the third rotation axis unit 230. Consequently, if the ring-shaped switch 510 rotates along the outer circumferential direction of the housing 231 in a state in which the projecting part 524 is fitted into the opening 232 and the opening 511, the projecting part 524 moves along the extension direction of the opening 232, and correspondingly, the second movable part 523 joined to the projecting part 524 moves along the drive shaft of the actuator 330 while also rotating about the drive shaft.

In other words, in the illustrated configuration, by causing the ring-shaped switch 510 to rotate along the outer circumferential direction of the housing 231 of the third rotation axis unit 230, the second movable part 523, via the projecting part 524, moves towards the first movable part 522, or in other words, in the positive x-axis direction of the drawing. A wave washer (not illustrated) that fulfills the function of a flat spring is provided between the opposing faces in the x-axis direction of the second movable part 523 and the first movable part 522, so that by causing the second movable part 523 to move in the positive x-axis direction, the first movable part 522 is pressed in the positive x-axis direction by the second movable part 523 through the wave washer. The conical surface of the first movable part 522 is pressed against the conical surface of the stationary part 521, and the cone brake 520 is engaged.

Note that the ring-shaped switch 510 is provided with a stopper 512 that restrains the rotation thereof, and the ring-shaped switch 510 is configured to be unable to rotate unless the stopper 512 is released (see FIG. 5). With this arrangement, a situation in which the ring-shaped switch 510 is rotated by an incorrect operation and the manual brake mechanism 50 malfunctions may be avoided.

The above thus describes a configuration of the manual brake mechanism 50 according to the second embodiment with reference to FIGS. 5 to 7. As described above, according to the second embodiment, there is provided a manual brake mechanism 50 capable of applying a brake to one rotation axis unit. In the case in which it is difficult to configure a manual brake mechanism that acts on multiple rotation axis units at the same time like the manual brake mechanism 40 according to the first embodiment, or in the case in which it is not necessary to configure a manual brake mechanism that acts on multiple rotation axis units at the same time, the manual brake mechanism 50 that acts on one rotation axis unit like in the second embodiment may be used favorably.

Note that even in the second embodiment, similarly to the first embodiment, a detection mechanism that detects whether the manual brake mechanism 50 has been engaged may be provided favorably in the microscope device 10. Additionally, in the case in which the detection mechanism detects that the manual brake mechanism 50 has been engaged, driving control of the actuator 330 by the control device 140 may be stopped. Also, a manual describing information such as how to use the manual brake mechanism 50 may be prepared.

Note that the configuration illustrated in FIGS. 5 to 7 is merely one example, and the second embodiment is not limited to such an example. In the second embodiment, it is sufficient to configure a manual brake mechanism that acts respectively on each of on one or multiple rotation axis units (in the illustrated example, the third rotation axis unit 230) considered to have insufficient braking force to maintain the attitude of the support unit 120, and the specific configuration may be designed appropriately.

3. Placement of Manual Brake Mechanism

As an example, the first embodiment above describes a case in which the second rotation axis unit 220 and the third rotation axis unit 230 are provided with the manual brake mechanism 40. Also, as an example, the second embodiment above describes a case in which the third rotation axis unit 230 is provided with the manual brake mechanism 50. However, the present disclosure is not limited to such an example. It is sufficient for a manual brake mechanism according to the present disclosure to be provided in order to maintain the attitude of the support unit 120, and to be provided with respect to a rotation axis unit that may rotate unintentionally due to the attachment of a member not anticipated during ordinary operation, such as the auxiliary observation device 30, in the case in which such a member is attached to the microscope unit 110 or the support unit 120 and upsets the balance of the support unit 120.

Specifically, the placement of the manual brake mechanism is decided by criteria like the following, for example.

A manual brake mechanism is provided favorably with respect to a rotation axis unit having a smaller braking force among the rotation axis units of the support unit 120. This is obviously because, in the case in which a member not anticipated during ordinary operation like the auxiliary observation device 30 is attached to the microscope unit 110 or the support unit 120, it is considered difficult for a rotation axis unit having a smaller braking force to support the increased rotation moment corresponding to the weight of the auxiliary observation device 30.

More specifically, the equilibrium between the magnitude of the rotation moment that each rotation axis unit should support and the braking force in each rotation axis unit when the attitude of the support unit 120 is maintained may be considered, and a manual brake mechanism may be provided with respect to each rotation axis unit for which the rotation moment is greater than the braking force of that rotation axis unit. Providing a manual brake mechanism with respect to a rotation axis unit corresponds to increasing the braking force in that rotation axis unit. Consequently, if a manual brake mechanism is provided with respect to such a rotation axis unit, and enough braking force to support the rotation moment is imparted to the rotation axis unit, the attitude of the support unit 120 is maintained.

Note that the magnitude of the rotation moment that each rotation axis unit should support is decided in accordance with the length (size), shape, and weight of the configuration disposed farther on the front end side than each rotation axis unit. Consequently, the magnitude of the rotation moment that each rotation axis unit should support when the auxiliary observation device 30 is attached can be computed on the basis of the configuration of the support unit 120. Since the value of the braking force in each rotation axis unit is known as part of the specifications of the electronically controlled brake mechanisms and the actuators, the rotation moment computation results and the values of the braking force in each rotation axis unit determined from the specifications can be utilized to decide which rotation axis units are to be provided with a manual brake mechanism.

Herein, like in the embodiments described above, there are cases in which, given an objective such as miniaturizing the configuration near the microscope unit 110 of the support unit 120 or reducing power consumption, a subset of the rotation axis units, particularly a rotation axis unit provided comparatively close to the microscope unit 110, is not provided with an electronically controlled brake mechanism and provided with only an actuator. A rotation axis unit provided close to the microscope unit 110 often is a rotation axis unit that may restrain the attitude of the microscope unit 110, or in other words, a rotation axis unit provided with only an actuator favorably may be a rotation axis unit that may restrain the attitude of the microscope unit 110 (in the case of the configuration illustrated in FIG. 1, the second rotation axis unit 220 and the third rotation axis unit 230).

In a case in which a flow of current is not being provided to the microscope device 10, such as during a loss of power, for example, the holding force of the motor in a rotation axis unit provided with only an actuator acts as a braking force that impedes rotation in that rotation axis unit. Typically, however, the holding force of a motor is less than the braking force in an electronically controlled brake mechanism (for example, an electromagnetic brake). In this way, a rotation axis unit not provided with an electronically controlled brake mechanism and provided with only an actuator is considered to have relatively less braking force than a rotation axis unit provided with an electronically controlled brake mechanism. Consequently, a manual brake mechanism may be provided with respect to a rotation axis unit for which the stoppage of rotation is controlled by the driving of an actuator and not with an electronically controlled brake mechanism.

4. Supplemental Remarks

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

A surgical microscope device, including:
a microscope unit that images an observation target, and outputs a picture signal;
a support unit that supports the microscope unit, and is configured as a balance arm; and
an auxiliary observation device that is attachable to the microscope unit or the support unit, in which
a manually operated manual brake mechanism is provided with respect to at least one of a plurality of rotation axis units constituting the support unit.

(2)

The surgical microscope device according to (1), in which
the manual brake mechanism is provided with respect to a rotation axis unit having a smaller braking force in a case in which the manual brake mechanism is not provided, from among the plurality of rotation axis units constituting the support unit.

(3)

The surgical microscope device according to (1) or (2), in which
the manual brake mechanism is provided with respect to a rotation axis unit in which a rotation moment that the rotation axis unit should support when maintaining an attitude of the support unit is greater than the braking force in the rotation axis unit in a case in which the manual brake mechanism is not provided.

(4)

The surgical microscope device according to any one of (1) to (3), in which
the manual brake mechanism is provided with respect to a rotation axis unit in which a stoppage of rotation is controlled by a driving of an actuator.

(5)

The surgical microscope device according to any one of (1) to (4), in which
the one manual brake mechanism is provided with respect to a plurality of the rotation axis units, and the one manual brake mechanism applies brakes to the plurality of the rotation axis units at a same time.

(6)

The surgical microscope device according to any one of (1) to (4), in which
the manual brake mechanism is provided with respect to one rotation axis unit, and applies a brake to the one rotation axis unit.

(7)

The surgical microscope device according to any one of (1) to (6), in which
the manual brake mechanism is made up of
a switch that is pressable in a certain direction, and
a friction brake that, by a movable part moving in the certain direction in conjunction with the switch and being pressed against a stationary part, produces a braking force due to friction at a contact surface between the movable part and the stationary part.

(8)

The surgical microscope device according to any one of (1) to (6), in which
the manual brake mechanism is made up of
a ring-shaped switch that is rotatable along an outer circumference of an arm unit constituting the support unit, and
a friction brake that, by a movable part moving in a certain direction in conjunction with the ring-shaped switch and being pressed against a stationary part, produces a braking force due to friction at a contact surface between the movable part and the stationary part.

(9)

The surgical microscope device according to any one of (1) to (8), in which
the auxiliary observation device is attached to the microscope unit or the support unit in a case in which a picture imaged by the microscope unit is not displayed normally on a display device, and
the manual brake mechanism operates in a case in which the auxiliary observation device is attached to the microscope unit or the support unit.

(10)

A surgical microscope system, including:
a microscope device that includes a microscope unit that images an observation target and outputs a picture signal, a support unit that supports the microscope unit and is configured as a balance arm, and an auxiliary observation device that is attachable to the microscope unit or the support unit; and
a display device that displays a picture based on the picture signal, in which
in the microscope device, a manually operated manual brake mechanism is provided with respect to at least one of a plurality of rotation axis units constituting the support unit.

REFERENCE SIGNS LIST

1 microscope system
10 microscope device
20 display device
30 auxiliary observation device
40, 50 manual brake mechanism
110 microscope unit
120 support unit (arm unit)
130 base unit
140 control device
210 first rotation axis unit
220 second rotation axis unit
230 third rotation axis unit
240 fourth rotation axis unit (parallelogram link mechanism)
250 fifth rotation axis unit
260 sixth rotation axis unit
241, 242, 243, 244 arm
245, 246, 247, 248 joint unit
271 first arm unit
272 second arm unit
273 third arm unit
274 fourth arm unit
275 fifth arm unit
320, 330 actuator
410 switch
420 cam slider
430, 440, 520 cone brake
510 ring-shaped switch

The invention claimed is:

1. A surgical microscope device, comprising:
a microscope that images an observation target and outputs a picture signal;
a support including a plurality of rotation axis points that supports the microscope and is configured as a balance arm, each of the plurality of rotation axis points including an associated first motor having a holding torque that automatically holds a position of the corresponding rotation axis point when power is lost;

an auxiliary device that is attachable to the microscope or the support, the auxiliary device to be rotated about a first rotation axis point of the plurality of rotation axis points; and a manual brake that stops rotation of at least one of the plurality of rotation axis points other than the first rotation axis point included in the support, the manual brake having a second motor with a smaller holding torque than a first motor associated with the first rotation axis point, and the manual brake stops the at least one of the plurality of rotational axis points other than the first rotation axis point to compensate for imbalance of the balance arm occurring due to attachment of the auxiliary device.

2. The surgical microscope device according to claim 1, wherein
the manual brake is provided with respect to a rotation axis point having a smaller braking force in a case in which the manual brake is not provided, from among the plurality of rotation axis points included in the support.

3. The surgical microscope device according to claim 2, wherein
the manual brake is provided with respect to a rotation axis point in which a rotation moment that the rotation axis point should support when maintaining an attitude of the support is greater than the braking force in the rotation axis point in a case in which the manual brake is not provided.

4. The surgical microscope device according to claim 3, wherein
the manual brake is provided with respect to a rotation axis point in which a stoppage of rotation is controlled by a driving of an actuator.

5. The surgical microscope device according to claim 1, wherein
the manual brake is provided with respect to the plurality of the rotation axis points other than the first rotation axis point, and the manual brake applies brakes to the plurality of the rotation axis points other than the first rotation axis point at a same time.

6. The surgical microscope device according to claim 1, wherein the manual brake is provided with respect to one rotation axis point, and applies a brake to the one rotation axis point.

7. The surgical microscope device according to claim 1, wherein the manual brake includes
a switch that is pressable in a certain direction, and
a friction brake that, by a movable part moving in the certain direction in conjunction with the switch and being pressed against a stationary part, produces a braking force due to friction at a contact surface between the movable part and the stationary part.

8. The surgical microscope device according to claim 1, wherein the manual brake includes a ring-shaped switch that is rotatable along an outer circumference of an arm included in the support, and
a friction brake that, by a movable part moving in a certain direction in conjunction with the ring-shaped switch and being pressed against a stationary part, produces a braking force due to friction at a contact surface between the movable part and the stationary part.

9. The surgical microscope device according to claim 1, wherein
the auxiliary device is attached to the microscope or the support in a case in which a picture imaged by the microscope is not displayed normally on a display device, and
the manual brake operates in a case in which the auxiliary device is attached to the microscope or the support.

10. The surgical microscope device according to claim 1, wherein the auxiliary device includes an auxiliary observation device.

11. The surgical microscope device according to claim 1, wherein the auxiliary device is to be rotated about the first rotation axis point of the plurality of rotation axis points even when power is lost.

12. The surgical microscope device according to claim 1, wherein the manual brake is controlled by an operator.

13. A surgical microscope system, comprising:
a microscope device that includes a microscope that images an observation target and outputs a picture signal, a support that supports the microscope and is configured as a balance arm, and an auxiliary device that is attachable to the microscope or the support; and
a display that displays a picture based on the picture signal,
wherein the support including a plurality of rotation axis points each including an associated first motor having a holding torque that automatically holds a position of the corresponding rotation axis point when power is lost,
wherein the auxiliary device is to be rotated about a first rotation axis point of the plurality of rotation axis points, and
in the microscope device, a manual brake is provided with respect to at least one of the plurality of rotation axis points other than the first rotation axis point included in the support, the manual brake having a second motor with a smaller holding torque than a first motor associated with the first rotational axis point, and
the manual brake stops the at least one of the plurality of rotational axis points other than the first rotational axis point to compensate for imbalance of the balance arm occurring due to attachment of the auxiliary device.

14. The surgical microscope system according to claim 13, wherein the auxiliary device includes an auxiliary observation device.

15. The surgical microscope system according to claim 13, wherein the auxiliary device is to be rotated about the first rotation axis point of the plurality of rotation axis points even when power is lost.

16. The surgical microscope system according to claim 13, wherein the manual brake is controlled by an operator.

* * * * *